United States Patent [19]

Wallach et al.

[11] Patent Number: 5,359,037
[45] Date of Patent: Oct. 25, 1994

[54] ANTIBODIES TO TNF BINDING PROTEIN I

[75] Inventors: David Wallach, Rehovot, Israel; Hartmut Engelmann, Munich, Fed. Rep. of Germany; Dan Aderka, Holon, Israel

[73] Assignee: Yeda Research and Development Co. Ltd., Rehovot, Israel

[21] Appl. No.: 563,151

[22] Filed: Aug. 6, 1990

Related U.S. Application Data

[63] Continuation-in-part of Ser. No. 243,092, Sep. 12, 1988, abandoned.

[30] Foreign Application Priority Data

Aug. 6, 1989 [IL] Israel ............................ 91229
Apr. 6, 1990 [IL] Israel ............................ 94039

[51] Int. Cl.$^5$ ............................................ C07K 15/00
[52] U.S. Cl. ..................... 530/388.22; 530/388.1; 530/389.1; 424/143.1; 424/172.1
[58] Field of Search .............. 530/389.1, 388.22, 866, 530/388.1; 424/85.8

[56] References Cited

FOREIGN PATENT DOCUMENTS 308378 3/1989 European Pat. Off. .
334165 9/1989 European Pat. Off. .

OTHER PUBLICATIONS

Wallach, David. "Cytotoxins (Tumour Necrosis Factor, Lymphotoxin and Others): Molecular and Functional Characteristics and Interactions with Interferons", in: *Interferon* 7 (Ion Gresser, Ed.), pp. 83–122, Acad. Press Ltd., London: 1986.

Beutler, B. and A. Cerami. "Cachectin: More Than a Tumor Necrosis Factor", in: *The New England Journal of Medicine*, vol. 316, No. 7, pp. 379–385 (1987).

Tracey, K. J. et al. "Shock and Tissue Injury Induced by Recombinant Human Cachectin", in: *Science*, vol. 234 (1986): 470–474.

Brockhaus, M. et al. "Identification of two types of tumor necrosis factor receptors on human cell lines by monoclonal antibodies", *Proc. Natl. Acad. Sci. USA*, vol. 87, No. 8, Apr. 1990: pp. 3127–3131.

Englemann, H. et al. "Two tumor necrosis factor-binding proteins purified from human urine," *J. Biol. Chem.* vol. 265, No. 3, Jan. 25, 1990: pp. 1531–1536.

Engelmann et al., J. Biol. Chem. 264: 11974–11980, 1989.

Olsson et al., Eur. J. Haematol. 42:270–275, 1989.

Seckinger et al., J. Biol. Chem 264: 11966–11973, 1989.

Maurer et al., Methods in Enzymology 70: 49–70, 1980.

Sevier et al., Clin Chem 27: 1797–1806, 1981.

Primary Examiner—Toni R. Scheiner
Assistant Examiner—Donna C. Wortman
Attorney, Agent, or Firm—Browdy and Neimark

[57] ABSTRACT

Antibodies to TNF Binding Protein I (TBP-I) are provided that can be used in diagnostic assays and as pharmaceutical agents for either inhibiting or mimicking the effects of TNF on cells.

6 Claims, 14 Drawing Sheets

ANTIBODIES TO TNF BINDING PROTEIN I

CROSS REFERENCE TO RELATED APPLICATION

The present application is a continuation-in-part of copending U.S. application Ser. No. 07/243,092, filed Sep. 12, 1988, now abandoned, the entire contents of which are hereby incorporated by reference.

FIELD OF THE INVENTION

This invention relates to antibodies against Tumor Necrosis Factor (TNF) Binding Protein I (hereinafter TBP-I) and to F(ab) fragments thereof, and to the use of said antibodies and fragments in diagnostic assays or as agents for either inhibiting or mimicking the effects of TNF on cells.

BACKGROUND OF THE INVENTION

Tumor Necrosis Factor (TNF-$\alpha$) and Lymphotoxin (TNF-$\beta$) (hereinafter, TNF refers to both TNF-$\alpha$ and TNF-$\beta$) are cytokines which have many effects on cells (Wallach, D. (1986) in: Interferon 7 (Ion Gresser, Ed.), pp. 83–122, Academic Press, London, and Beutler, B. and Cerami, A. (1987) New England J. Med. 316: 379–385). Both TNF-$\alpha$ and TNF-$\beta$ initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against infectious agents and to recovery from injury. But, quite clearly, both TNF-$\alpha$ and TNF-$\beta$ have also effects which can be extensively deleterious. There is evidence that overproduction of TNF-$\alpha$ can play a major pathogenic role in several diseases. Thus effects of TNF-$\alpha$, primarily on the vasculature, are now known to be a major cause for symptoms of septic shock (Tracey, K. J. et al. (1986) Science 234: 470–474). In some diseases, TNF may cause excessive loss of weight (cachexia) by suppressing activities of adipocytes and by causing anorexia and TNF-$\alpha$ was thus called cachectin.

There is therefore a necessity in finding out ways to eliminate or antagonize endogenously formed or exogenously administered TNF. One attempt in this direction was the isolation from human urine of the TNF Binding Protein called TBP-I and shown to be able to antagonize the effects of TNF. This antagonism was determined both by measuring reduction of the cytotoxic activity of TNF, as well as by measuring interference of TNF binding to its receptors.

The protein TBP-I was first described in our U.S. Patent application Ser. No. 07/243,092 filed on Sep. 12, 1988, in which was disclosed a process for its purification to homogeneity from human urine by chromatography on CM-Sepharose followed by high performance liquid chromatography (HPLC) on Mono Q and Mono S columns and reversed-phase HPLC. The homogeneous TBP-I thus obtained had an apparent molecular weight of about 27,000 in sodium dodecyl sulfate (SDS)-polyacrylamide gel electrophoresis (PAGE) under both reducing and nonreducing conditions. Homogeneity of the purified protein was confirmed by microsequence analysis which revealed a single N-terminal sequence: Asp-Ser-Val-Cys-Pro-.

TBP-I was shown to protect cells from TNF toxicity at concentrations of a few nanograms per ml and to interfere with the binding of both TNF-$\alpha$ and TNF-$\beta$ to cells, when applied simultaneously with these cytokines. Further examination of the mechanism by which TBP-I functions revealed that TBP-I does not interact with the target cell, but rather blocks the function of TNF by binding TNF specifically, thus competing for TNF with the TNF receptor.

Consequently to this finding we attempted an alternative approach for the purification of TBP-I, whereby urinary proteins or fractions thereof were applied on a column of immobilized TNF and, after removal of unbound proteins, the proteins which bound to the column were eluted, in bioactive form, by a decrease of the pH. In SDS PAGE analysis, most of the protein in the eluate migrated as a single broad band with apparent molecular size of 30,000±2,000.

When applied to further fractionation by reversed-phase HPLC, the proteins eluting from the TNF column showed the presence of two active components: one, TBP-I, eluting as expected at 27% acetonitrile and, in addition, a second TNF-binding protein, called TBP-II, eluting at a somewhat higher acetonitrile concentration (31%). Both proteins provide protection against the in vitro cytocidal effect of TNF and both bind TNF-$\beta$ less effectively than TNF-$\alpha$. Although in SDS PAGE analysis the two proteins, TBP-I and TBP-II, appeared to have a very similar molecular size, they could clearly be distinguished from each other by lack of immunological cross reactivity, differing N-terminal amino acid sequences and differing amino acid compositions. TBP-I and TBP-II are structurally related to two molecular species of the cell surface TNF receptors, the type I and type II receptors, respectively.

SUMMARY OF THE INVENTION

The present invention provides polyclonal and monoclonal antibodies specific for the TNF-binding protein TBP-I which have the following properties:

a) they block the effect of TNF on specific cells. This blocking effect is obtained using the antibodies or F(ab) fragments thereof, taking advantage of the ability of said antibodies to block the binding of TNF to cells, apparently through interaction with structurally related cell surface TNF-binding proteins, i.e. TNF receptors; and b) they mimic certain effects of TNF on specific cells. This mimicking effect of the antibodies is most likely due to activation of the receptors for TNF, upon their juxtaposition by the divalent antibodies, in a way which is similar to their activation by TNF itself.

The invention also comprises salts, functional derivatives and active fractions of the antibodies and of the F(ab) fragments thereof. As used herein, the term "salts" refers both to salts of carboxyl groups and to acid addition salts of amino groups of the protein molecule. "Functional derivatives" as used herein covers derivatives which may be prepared from the functional groups which occur as side chains on the residues or the N- or C-terminal groups, by means known in the art. As "active fractions" of the antibodies and their F(ab) fragments, the present invention covers any fragment or precursors of the polypeptide chain of said protein molecules alone or together with associated molecules or residues linked thereto, e.g. sugar or phosphate residues, or aggregates of the protein molecule or the sugar residues by themselves.

The invention further relates to the use of said antibodies and of F(ab) fragments thereof, and salts, functional derivatives or active fractions of said antibodies and fragments, as pharmaceutical agents both for mimicking and blocking effects of TNF on part or all cells in the human body.

Another aspect of the invention features the diagnostic use or tests for measuring either the TBP-I or the antisera against it, based on determining the interaction of the antibodies with the TBP-I. These diagnostic uses are of two kinds: (a) detecting endogenously produced antibodies to TBP-I in body fluids, to determine the extent to which such antibodies, by mimicking or blocking the effects of TNF, contribute to pathological manifestations of diseases, and (b) quantifying the levels of TBP-I in body fluids to detect or measure over- or under-production of this protein in any disorder characterized by abnormal production of said protein.

DETAILED DESCRIPTION OF THE INVENTION

Figure 1B:
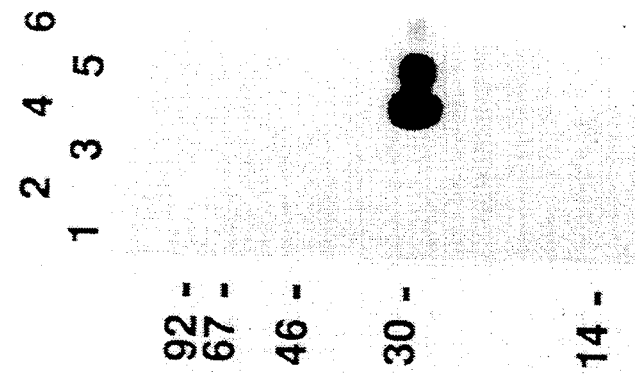
FIGS. 1A and 1B shows the Western blot analysis of the binding of rabbit antisera to TBP-I and TBP-II to the two species of TBP.

The antibodies of the present invention provide a new approach for the modulation of the TNF activity, and may be used both to inhibit and to mimic effects of TNF on specific subsets of cells, depending on the molecular form of the antibodies, specifically on their valence: monovalent forms of the antibodies (e.g. F(ab) fragments) being inhibitory and multivalent forms being able to mimic at least part of the effects of TNF. They are, thus, suitable as pharmaceutical agents both for mimicking and blocking TNF effects on cells.

The functional interaction of the antibodies of the present invention with TBP-I provides also a new diagnostic tool, based on immunoassays such as radioimmunoassay, ELISA etc., for the detection of over- or under-production of TBP-I by cells in the body in certain disorders. Thus, the level of TBP-I in sera of patients with different types of cancer or suffering from autoimmune disorders, such as systemic lupus erythematosus (SLE), can be determined this way. In an inverse approach, antibodies against TBP-I, when produced endogenously in the body, will be measured with the use of purified TBP-I. Detecting such autoantibodies, when formed in certain autoimmune disorders, is of extreme importance, since their ability to mimic or inhibit the effects of TNF surely has far-reaching bearing on the pathological syndromes of said disorders.

The antibodies may be either polyclonal or monoclonal. They may be raised in rabbits, mice or other animals or tissue cultured cells derived thereof or can be products of cells of human origin. They may also be produced by recombinant DNA technology either in a form identical to that of the native antibody or as chimeric molecules, constructed by recombination of antibody molecules of man and animal origins or in other forms chosen to make the antibodies most suitable for use in therapy.

For the preparation of the antibodies, either purified TBP-I or one or more synthetic peptides identical to the known sequence of a fragment thereof, e.g. to the N-terminal protein sequence, may be used to immunize animals. A further possibility is to fuse one of the possible nucleotide sequences coding for a fragment of TBP-I to the gene coding for Protein A, to express the fused Protein A-TBP-I gene in *E. coli*, to purify the fused protein by affinity chromatography on IgG Sepharose column and then to use it to immunize animals.

The monoclonal antibodies of the present invention are prepared using conventional hybridoma technique (Kohler et al. (1975) Nature 256:495; Kohler et al. (1976) Eur. J. Immunol. 6:511). After immunization, spleen cells alone or together with lymph node cells of the immunized animals are isolated and fused with a suitable myeloma cell line. After fusion, the resulting hybridoma cells are selectively maintained in HAT medium and then cloned. The hybridoma cells obtained through such a selection are then assayed to identify clones which secrete antibodies capable of binding TBP-I. After identification, the desired clones are grown in bulk, either in suspension culture or in ascitic fluid, by injecting the cells into the peritoneum of suitable host mice. The monoclonal antibodies produced by the hybridomas are then isolated and purified.

The monoclonal antibodies may also be immobilized and used for the purification of the TBP-I in affinity purification procedure using an immunoadsorbent column.

The antibodies of the invention are found to inhibit the binding of TNF to cells. Antisera to TBP-I block the binding of TNF to the cervical carcinoma HeLa cells and to the breast carcinoma MCF7 cells, but not to the histiocytic lymphoma U937 cells, while antisera against TBP-II have the inverse specificity. In the chronic myeloid leukemia K562 cells both antisera have inhibitory effects.

F(ab) fragments of the anti-TBP-I antibodies are found to block the effect of TNF on cells of a line to which TNF binding is blocked by the antiserum comprising said antibodies. However, the intact antibody molecules are found to exert the inverse effect; they by themselves elicit in cells a cytotoxic effect identical to the effect induced by TNF. This ability of antibodies apparently directed against cell surface receptors to mimic the effect of the agonist, as opposed to the lack of ability of the F(ab) fragments of the antibody to do so, is mostly a consequence of the ability of the divalent antibody molecule to cause clustering of the receptor molecules. This clustering somehow results in activation of the receptors in a way which is similar or identical to the activation of the receptors by TNF itself. Whatever the mechanisms involved, the fact that the antibodies can either mimic or inhibit the function of TNF, depending on the exact molecular form of the antibody applied, implies that these antibodies can practically serve as inhibitory or mimicking agents to TNF. Furthermore, since the antibodies to TBP-I and TBP-II bind to two different receptors for TNF, which are expressed on different cells exhibiting different responses to TNF and perhaps having also a different function even when expressed in the same cell, these inhibitory and mimicking effects of the antibodies to TBP-I and TBP-II can be applied for modulating the response to TNF, i.e. augmenting specifically beneficial effects and suppressing specifically deleterious effects of this cytokine.

As mentioned before, TBP-I and TBP-II are structurally related to the type I and type II cell surface receptors, respectively. The antibodies to TBP-I and TBP-II block specifically the binding of TNF to one of the two receptors and can be applied to immunoprecipitate the receptors. The antibodies to TBP-I also induce effects characteristic of TNF in cells which express the immunologically cross-reactive cell surface receptors.

The present invention further relates to pharmaceutical compositions comprising a pharmaceutically acceptable carrier and an antibody to TBP-I or an F(ab) fraction thereof or salts, functional derivatives, precursors or active fractions thereof or mixtures of any of the foregoing, as active ingredient. The way of administration can be via any of the accepted modes of administration for similar agents and will depend on the condition to be treated. The pharmaceutical compositions are prepared for administration by mixing the protein or its derivatives with physiologically acceptable carriers, stabilizers and excipients, and prepared in dosage form, e.g. by lyophilization in dosage vials. The amount of active compound to be administered will depend on the route of administration, the disease to be treated and the condition of the patient.

The invention will now be illustrated by the following non-limiting examples:

EXAMPLE 1: PURIFICATION OF TBP-I

1.1 Preparation of the urine concentrate

A pool of 200 l urine from healthy male donors or from healthy postmenopausal women was subjected to microfiltration on a Pellicon membrane with a pore size of 0.45 $\mu$m. The filtrate was concentrated by ultrafiltration using a Pellicon membrane with a molecular weight cut-off of 10 kDa to a final volume of 500 ml. The concentrate was dialyzed against phosphate buffered saline containing 1 mM benzamidine and 0.1% sodium azide.

1.2 Affinity purification of TBP-I on a column of immobilized TNF

Recombinant TNF-$\alpha$ was brought to a concentration of 7.2 mg/ml, then equilibrated with PBS containing 0.02% sodium azide and coupled to Affigal 10 (3.6 mg to 0.5 ml beads). A sample of 250 ml of the concentrate of urinary proteins of step 1.1 was applied to a column constructed from the beads of the immobilized TNF at a flow rate of 0.2-0.3 ml/min. at 4° C. Unbound proteins were removed by washing with PBS and the bound proteins were then eluted by applying a solution of 25 mM citric acid, 100 mM NaCl and 0.02% sodium azide, at pH 2.5. The specific bioactivity (inhibition of TNF toxicity) of the eluted proteins was about 20,000 fold higher than that of the crude urinary proteins. In SDS PAGE analysis most of the protein in the eluate migrated as a single broad band with apparent molecular size of about 30,000±2,000.

1.3 Reversed-phase high pressure liquid chromatography (HPLC)

Further fractionation of the affinity purified proteins of step 1.2 was by reversed-phase HPLC on an Aquapore RP300 column (4.6×30 mm, Brownlee Labs), first preequilibrated and then washed with 0.3% aqueous trifluoroacetic acid (TFA) (Buffer F) until a stable baseline was obtained by the fluorescamine detection system. Pooled active fractions eluted from the affinity TNF column of step 1.2 were applied on the column, elution was performed at a flow rate of 0.5 ml/minute with linear gradients of acetonitrile in Buffer F (0-20% for 5 minutes, followed by 20-50% for 60 minutes and finally 50-80% for 5 minutes), and then the column was washed for 15 minutes with 80% acetonitrile. TBP-I eluted between 26% and 29% acetonitrile and TBP-II between 29% and 32% acetonitrile concentration.

EXAMPLE 2: Preparation of Polyclonal Antibodies against TBP-I

For the immunization of rabbits, the animals were first injected subcutaneously with 5 $\mu$g of TBP-I as emulsion in complete Freund adjuvant. Three weeks later they were injected again, intramuscularly, as emulsion in incomplete Freund adjuvant and then twice again subcutaneously as solution in PBS, at one week intervals. The rabbits were bled 10 days after the last immunization.

For the purification of immunoglobulins from the rabbit serum, saturated ammonium sulfate was added to 10 ml serum to a final concentration of 50% saturation. After overnight incubation at 4° C., the immunoglobulins were precipitated by centrifugation. The pellet was washed twice with 50% ammonium sulfate, then solubilized in 10 mM sodium borate 0.02% sodium azide at pH 9. The solution was then dialyzed extensively against the borate-azide solution. It was then applied for chromatography on HPLC Mono-Q column, from which the proteins were eluted with a gradient of 0–500 mM NaCl in the above borate-azide solution. The immunoglobulins eluted at a salt concentration of approximately 70 mM NaCl.

The antiserum to TBP-I suppressed the binding of $^{125}$I-TNF to HeLa cells by about 50% at a dilution of 1:6400. Antiserum to TBP-II was raised in rabbits in the same conditions and was shown to suppress the binding of $^{125}$I-TNF to U937 cells at a similar dilution. The extent of the immunological crossreactivity of both antisera were examined by Western blot analysis. It showed that TBP-I and TBP-II are immunologically distinct: each antiserum recognized significantly only that species of TBP against which it had been raised.

For the Western blot analysis, the tested proteins were applied to SDS PAGE on 10% acrylamide gels and then blotted electrophoretically to a nitrocellulose sheet. The nitrocellulose sheet was incubated with 10% milk (v/v) in PBS, then briefly rinsed in PBS and further incubated with the tested antibodies in a multi-lane device. After incubation with either $^{125}$I-labelled Protein A or $^{125}$I-goat antimouse F(ab) fragments of IgG, both at $5.10^5$ CPM/ml, the unbound material was washed and the nitrocellulose sheet was exposed to autoradiography.

Figure 1A:
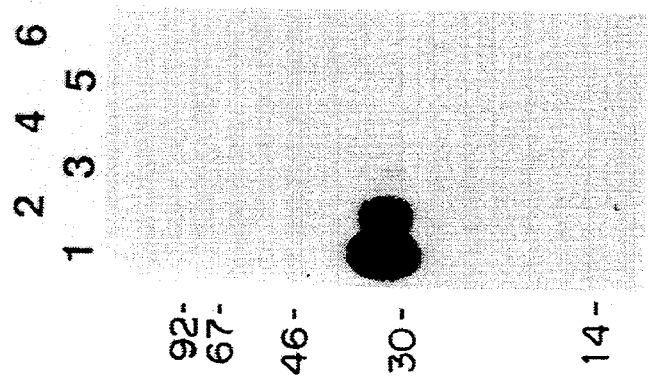
Figure 2:
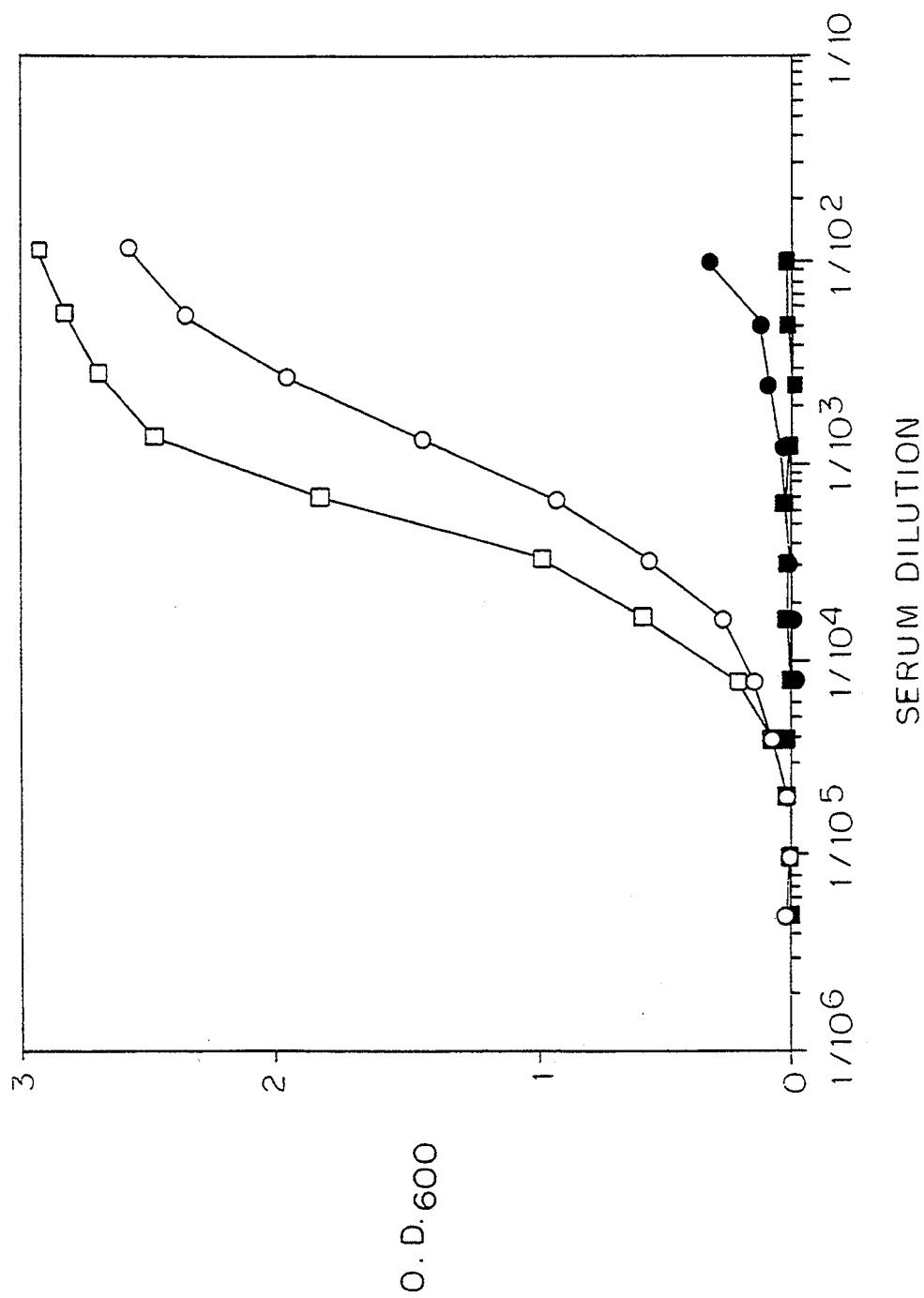
FIG. 2 shows ELISA for the binding of rabbit antisera against TBP-I and TBP-II to the two species of TBP.

FIGS. 1A and 1B show the Western blot analysis of the binding of antisera against TBP-I and TBP-II to the two proteins. TBP-I (FIG. 1A: lanes 1–6) and TBP-II (FIG. 1B: lanes 1–6) were applied to SDS PAGE at 2 μg/lane together with 2 μg BSA. Following electrophoresis the proteins were blotted electrophoretically to a nitrocellulose sheet which was then incubated with antiserum to TBP-I (lanes 1–3) or to TBP-II (lanes 4–6) at the following dilutions: lanes 1,4–1:100; lanes 2,5–1:500; lanes 3,6–1:2500. After incubation with the antibodies, the nitrocellulose sheet was incubated with $^{125}$I-labelled protein A and then washed and exposed to autoradiography. Similarly, when examining the interaction of the antisera and the proteins in ELISA, the antiserum against TBP-I was found to react with TBP-I at a dilution of up to 1:25,000, but did not react with TBP-II, not even at a dilution of 1:100. FIG. 2 shows the results of ELISA for the binding of antisera against TBP-I and TBP-II to the two species of TBP. The binding of (□) antiserum against TBP-I to TBP-I, (■) antiserum against TBP-I to TBP-II, (●) antiserum against TBP-II to TBP-I, and (o) antiserum against TBP-II to TBP-II, is presented in terms of the absorbance of the color product in the horseradish peroxidase assay. The readings in a control test at which the antibodies were applied on wells coated with BSA were subtracted. (The slight binding of the antiserum against TBP-II to TBP-I, observed in FIG. 2, could be shown to be due to contamination of the antiserum with antibodies to TBP-I, at low amounts, due to the presence of some TBP-I in the preparation of TBP-II used for immunization).

EXAMPLE 3: Effects of the polyclonal Antibodies on Binding of TNF to Cells

The antisera to TBP-I and TBP-II were diluted in Dulbecco's balanced salt solution (PBS+) containing 0.5% BSA and 0.1% sodium azide (PBS/BSA) and then either directly or, in competition experiments, after incubation with a sample of TBP, applied for 2 h on the tested cells of the HeLa, MCF7, K562 and U937 cell lines. The cells were then rinsed and tested for binding of TNF.

Figure 3:
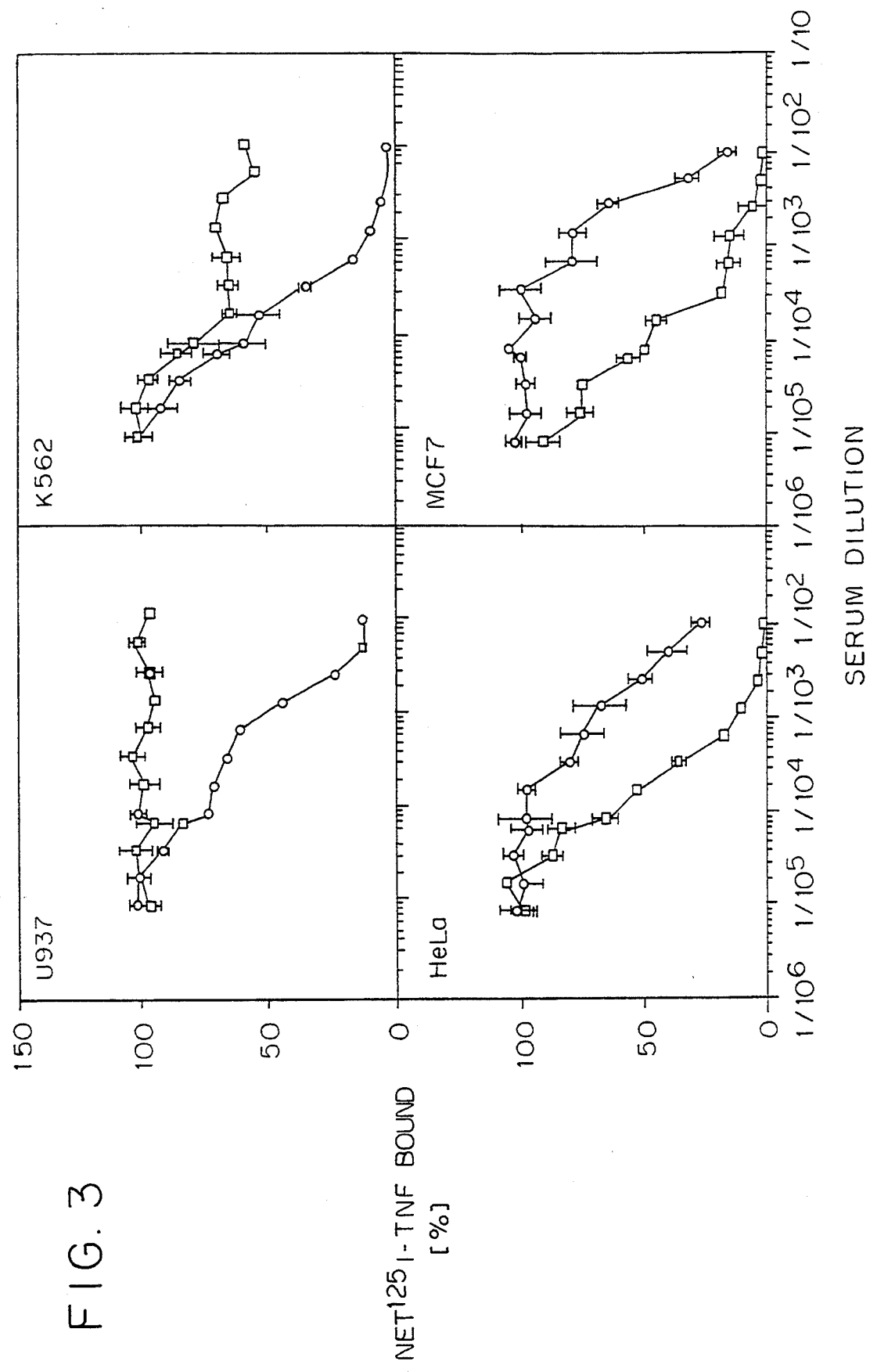
FIG. 3 shows the inhibition of the binding of radiolabelled TNF to different cell lines with rabbit antisera to TBP-I and TBP-II.

FIG. 3 shows the inhibition of the binding of radiolabelled TNF to U937, K562, HeLa and MCF7 cells with antisera to TBP-I (o) and TBP-II (□). The net binding observed in the absence of antisera (100%) was in U937 cells - 2500 CPM, in K562 cells - 1500 CPM, in HeLa cells - 2400 CPM and in MCF7 cells - 1100 CPM. The results demonstrate that antisera against TBP-I and TBP-II interfere with the binding of TNF to cells, each affecting to different extent cells of different lines. The antiserum against TBP-I inhibits effectively the binding of TNF to HeLa and MCF7 cells, but has no effect on the binding of TNF to U937 cells and only little effect on the binding of TNF to K652 cells. Inversely, the antiserum against TBP-II blocks effectively the binding of TNF to the K562 and U937 cells, but inhibits the binding of TNF to the HeLa and MCF7 cells only at high concentrations. The effect of the antiserum against TBP II on the latter cells could be shown, by competition experiments, in which pure TBP-I and TBP-II were added to the serum, to be due to the presence of contaminating antibodies to TBP-I in this preparation of antiserum to TBP-II.

EXAMPLE 4: F(ab) Fragments of Polyclonal Antibodies to TBP-I

Immunoglobulins purified from the antiserum to TBP-I were exposed to digestion with papain, in the presence of cysteine/EDTA at an enzyme/ substrate ratio of 1:100. The antibody digest was dialyzed against 10 mM sodium acetate buffer, pH 5.5 and subjected to cation exchange HPLC on a Mono-S column. The bound proteins were eluted from the Mono-S column with a 0.300 mM gradient of NaCl in 10 mM sodium acetate buffer, which resulted in purification of the F(ab) fragments to homogeneity. Furity was verified by SDS PAGE analysis under reducing and non-reducing conditions. To test the effect of these fragments on the cytocidal activity of TNF, they were applied on HeLa cells, the cells were then rinsed to remove all unbound antibodies and exposed for 10 h to TNF, together with cycloheximide (25 μg/ml). Viability of cells was then determined by the neutral red uptake method.

Figure 4:
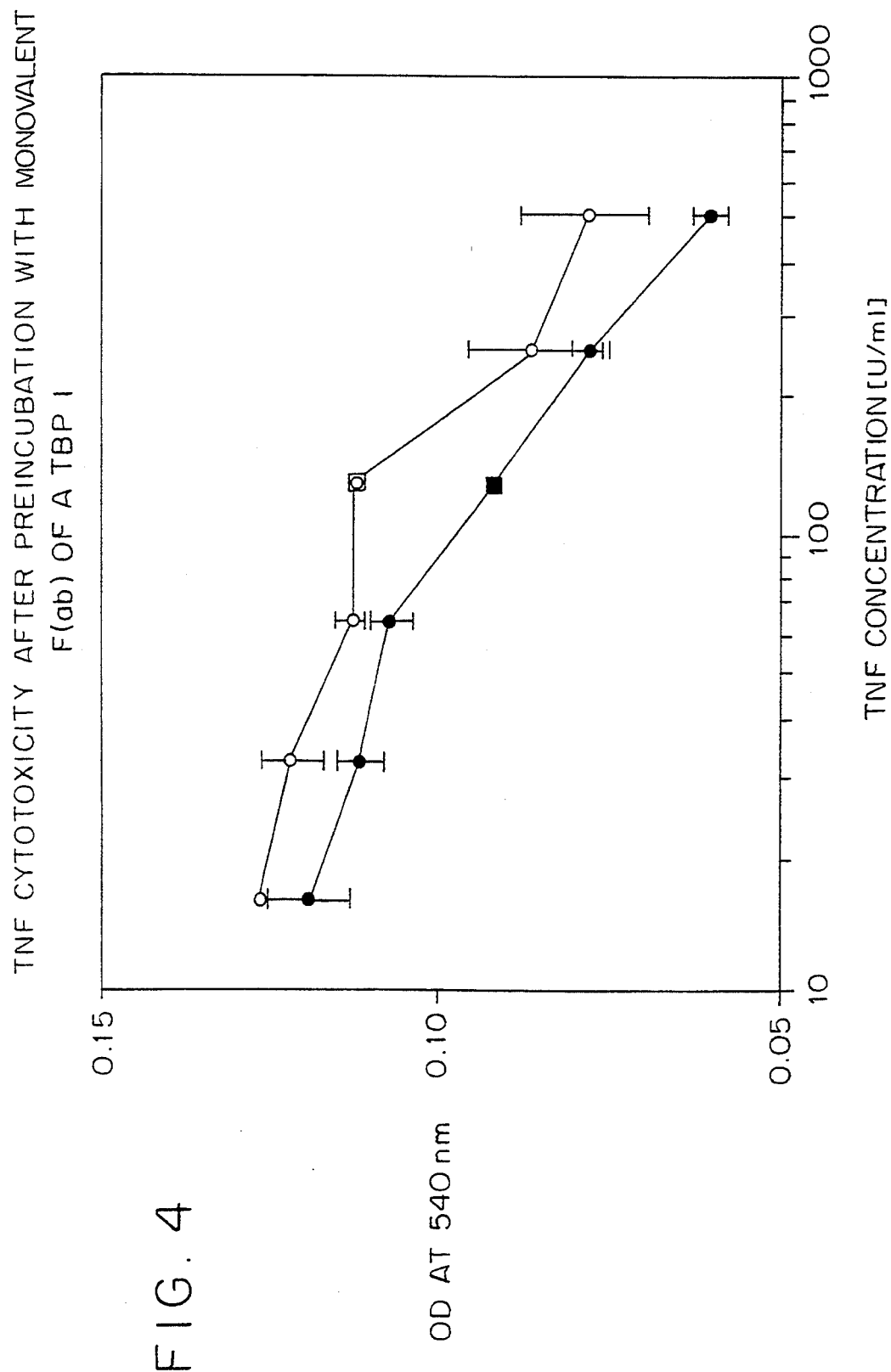
FIG. 4 shows the protection of cells from TNF cytotoxicity after preincubation with monovalent F(ab) fragments of antibodies to TBP-I.

In FIG. 4: Protection from TNF cytotoxicity by the monovalent fregments of the antibodies to TBP-I: HeLa cells which were pretreated with the F(ab) fragments (3 μg/ml) (●) and, for comparison, cells treated in the same way with medium alone, (o) were further incubated for 10 h with TNF, at various concentrations, together with CHI (25 μg/ml). The results show that the F(ab) fragments of the antibodies to TBP-I protect HeLa cells from the cytocidal effect of TNF - a reflection of the fact that they interfere with the binding of TNF to the TNF receptors expressed on the surface of these cells.

Figure 9A:
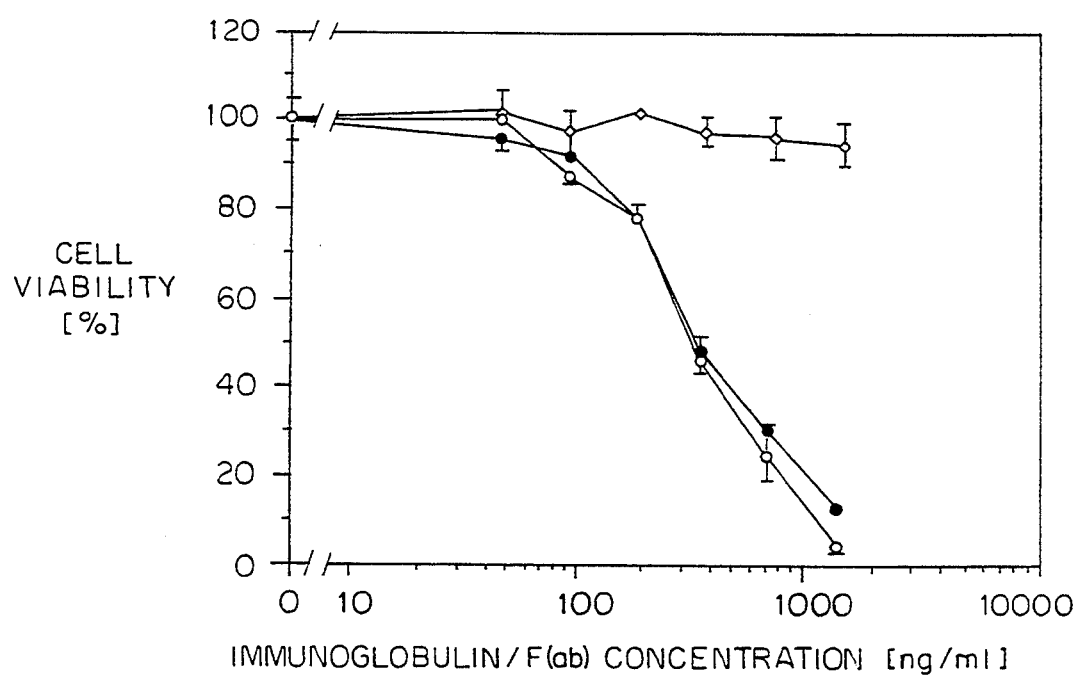
FIGS. 9A, 9B, and 9C shows the lack of cytocidal activity in monovalent F(ab) fragments of the antibodies to TBP-I and recovery of that activity by cross-linking the F(ab) fragments with anti-immunoglobulin antibodies.
Figure 9B:
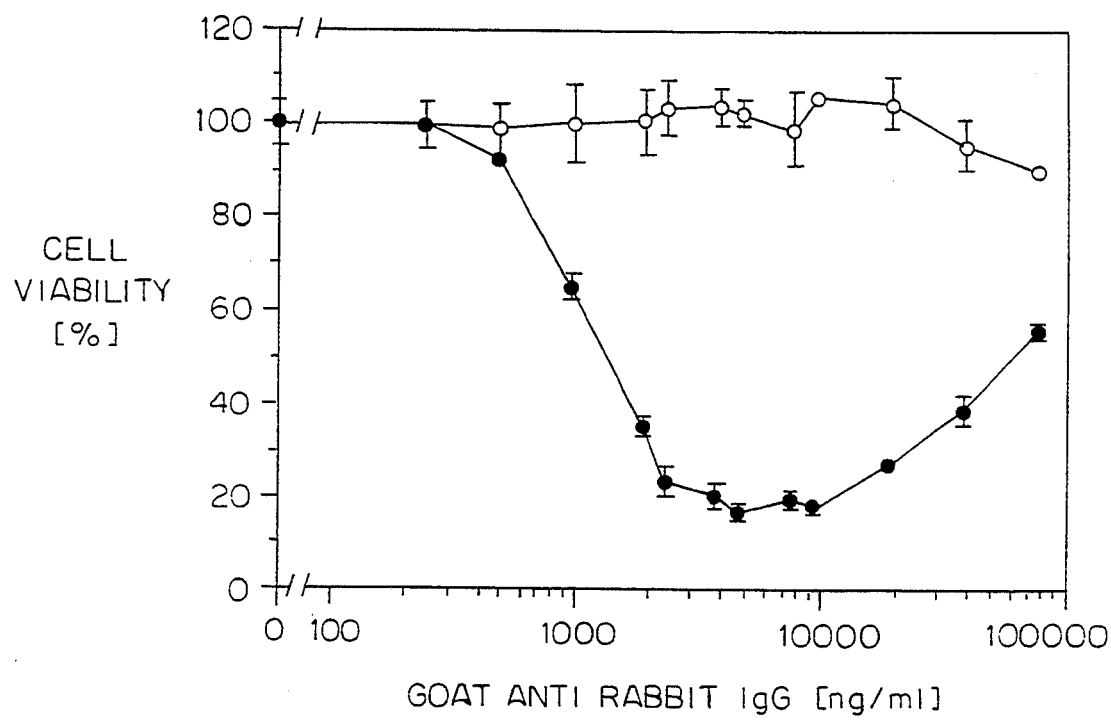
Figure 9C:
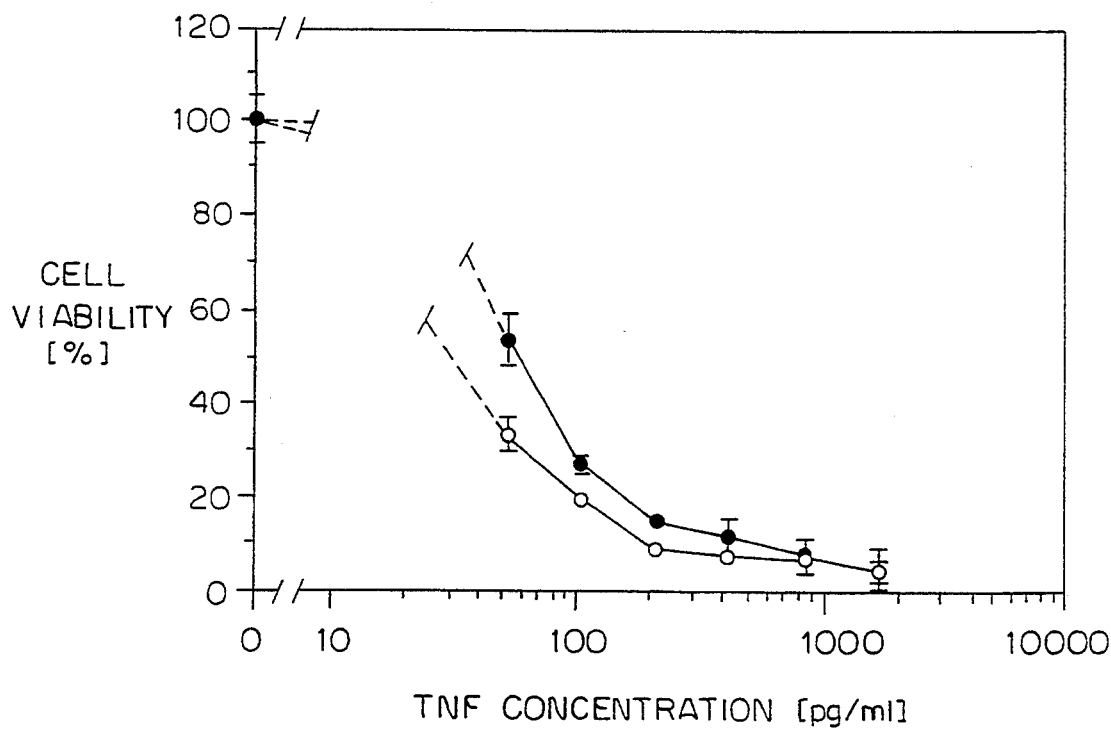
Figure 10A:
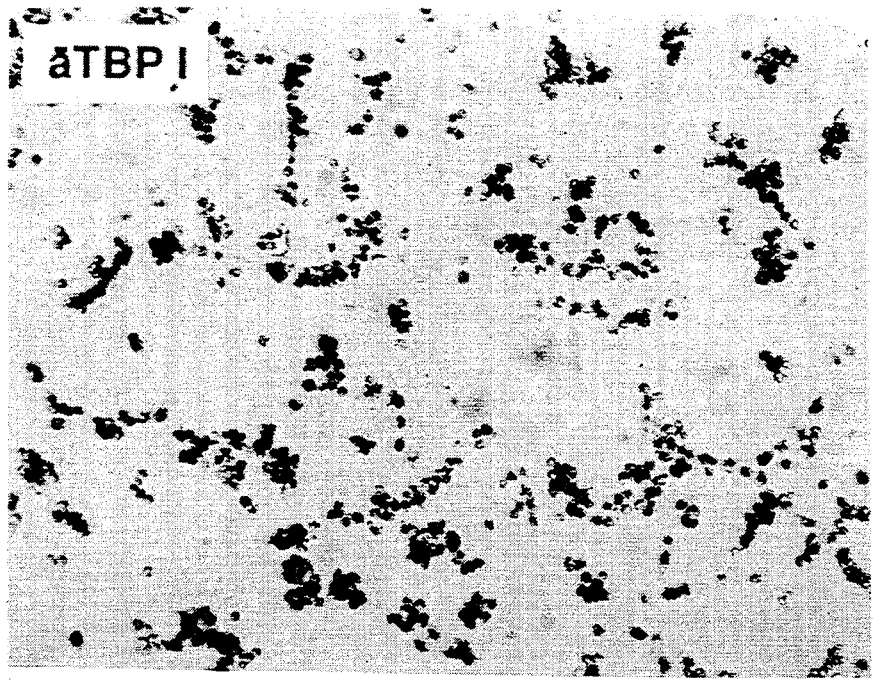
FIGS. 10A, 10B, 10C and 10D shows the morphology of SV80 cells after "pulse" treatment with monovalent F(ab) fragments of antibodies to TBP-I and further incubation in the presence or absence of anti-immunoglobulin antibodies.
Figure 10B:
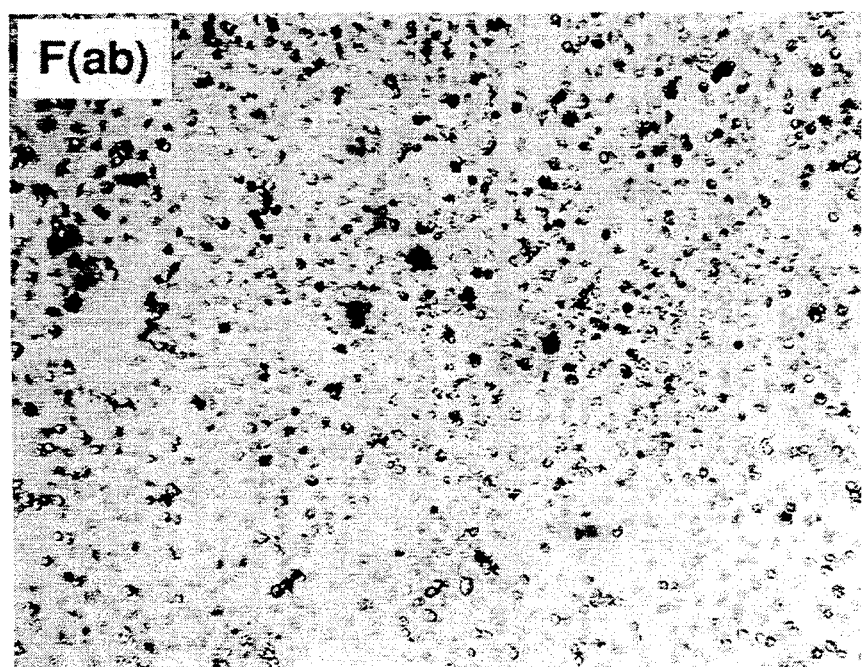
Figure 10C:
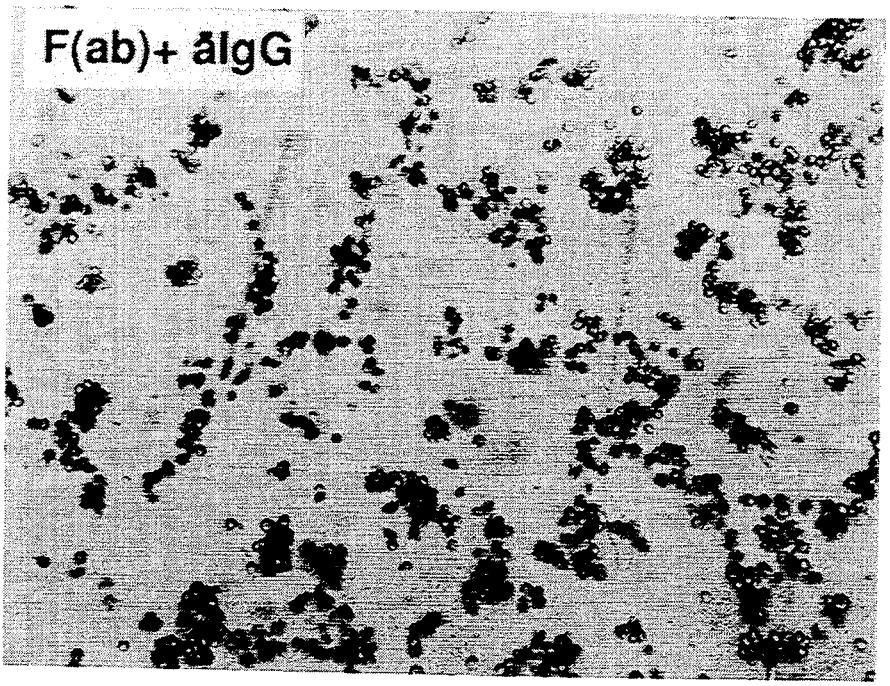
Figure 10D:
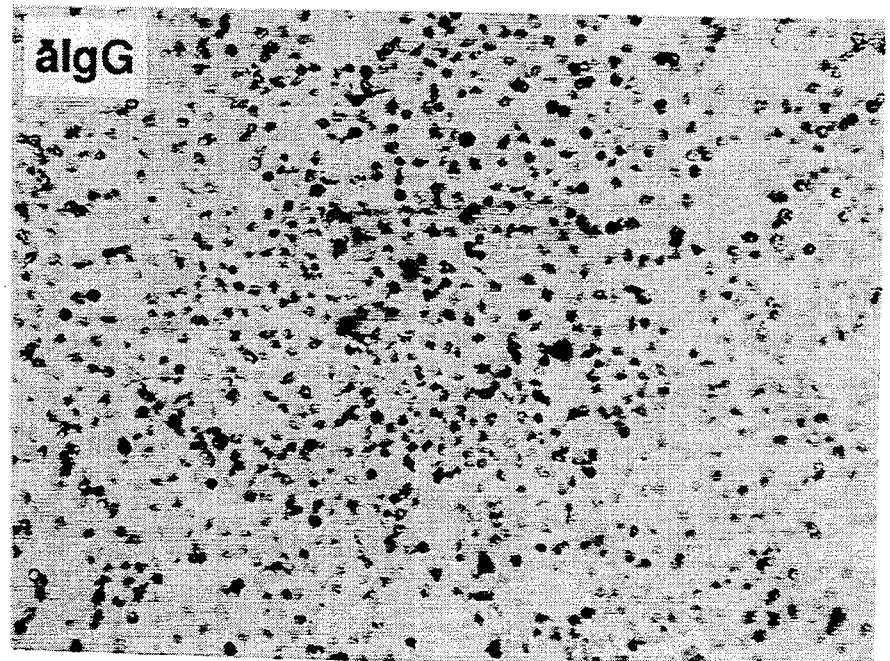

Similar results were obtained when the F(ab) fragments were applied on SV80 cells as illustrated in FIG. 9C, described in detail under Example 5, section f, below.

Table I shows that in the intact state antibodies to TBP-I have the inverse effect to that mediated by their F(ab) fragments; namely, they minic the effect of TNF and are by themselves cytotoxic.

TABLE I

TNF-like cytocidal effect of antibodies to TBP-I

| TNF (μ/ml) | Cell Viability (%) |
|---|---|
| — | 100 |
| 1 | 31 |
| 10 | 15 |
| 100 | 6 |
| 1000 | 3 |
| anti TBP serum (dilution) | |
| 1:6400 | 69 |
| 1:1600 | 37 |
| 1:400 | 17 |
| 1:100 | 9 |

TNF and the antiserum to TBP-I were applied on SV80 cells for 12 h together with cycloheximide. Viability of the cells was then determined by the neutral red uptake method (see also FIG. 5).

EXAMPLE 5: Determination of Bioactivities of the Antibodies to TBP-I a. Cytotoxic activity

Cells were seeded 24 hr prior to assay in 96 well (microtiter plates) ($3 \times 10^4$ cells/well). The antibodies to TBP-I or TNF were applied in serial dilutions either in the presence or the absence of cyclohexi- mide (CHI) (25 μg/ml in the case of the HeLa cells and 50 μg/ml for the other cells). After an incubation period of 12 hr for the HeLa cells and 16 hr for all the others, cell viability was determined by the neutral-red uptake method. Cell viability is presented as the per cent ratio of the viability of cultures incubated with CHI alone (for cells tested in its presence) or without additives.

Figure 5A:
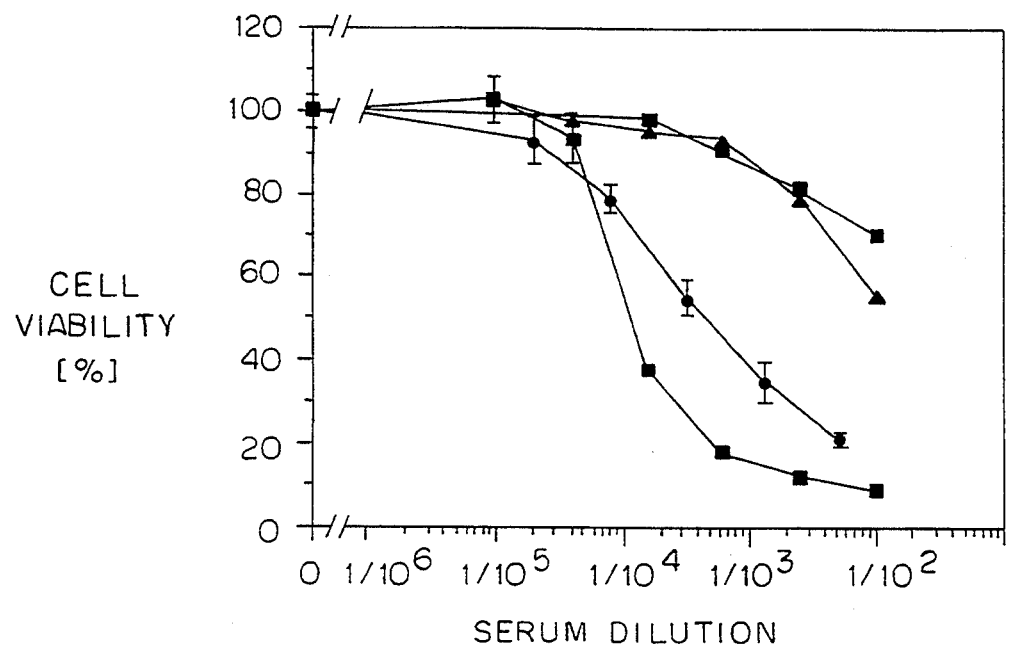
FIGS. 5A and 5B shows the cytocidal effect of antibodies to TBP-I (A) and of TNF (B) on different cell lines.
Figure 5B:
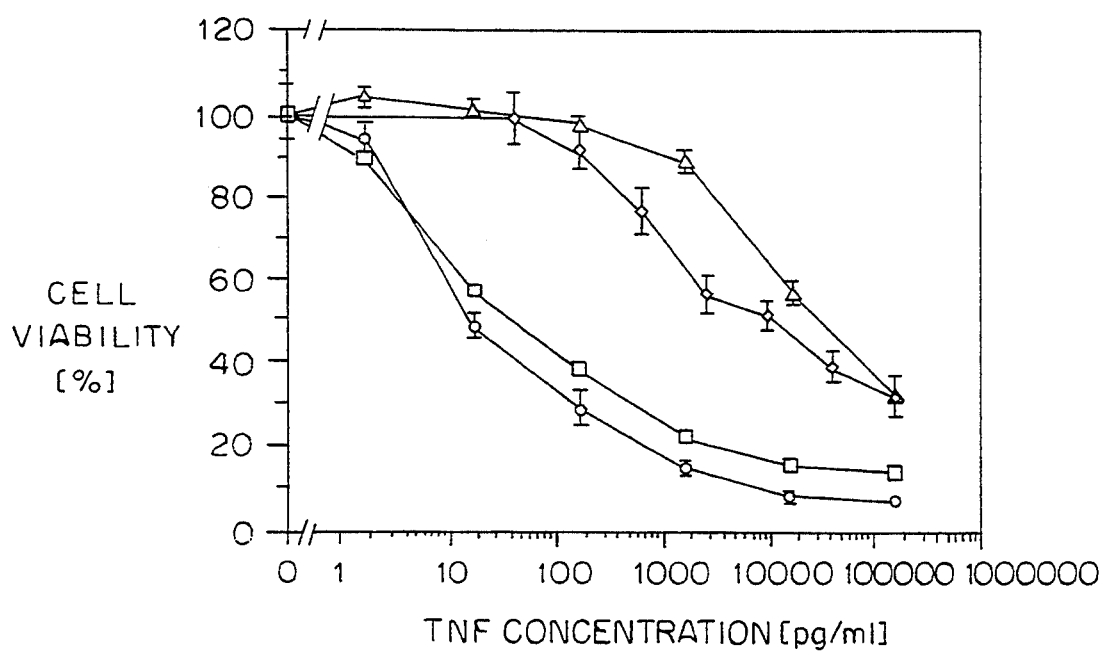

FIGS. 5A and 5B show the cytocidal effect of the antibodies to TBP-I (FIG. 5A) and of TNF (FIG. 5B) on SV80 (o,●) HeLa (□, ■), FS11 (△, ▲) and HEp-2 (◇,◆) cells. The antibodies and TNF were applied for 16 hr (12 hr for HeLa cells) together with CHI (25 μg/ml for HeLa and 50 μg/ml for all other cells). Cell viability was quantitated by measuring the uptake of neutral red dye. Viability of cells incubated with anti TBP-I at 1:200 in the absence of CHI was 99% in the SV80 cells, 97% in HeLa cells, 98% in FS11 cells and 96% in the HEp-2 cells. Normal rabbit serum in the range of concentrations of anti-TBP-I applied in this study had no effect in this experiment or in any of the other experiments presented below. All tests were performed in duplicates.

b. Induction of PGE₂ synthesis

Figure 6:
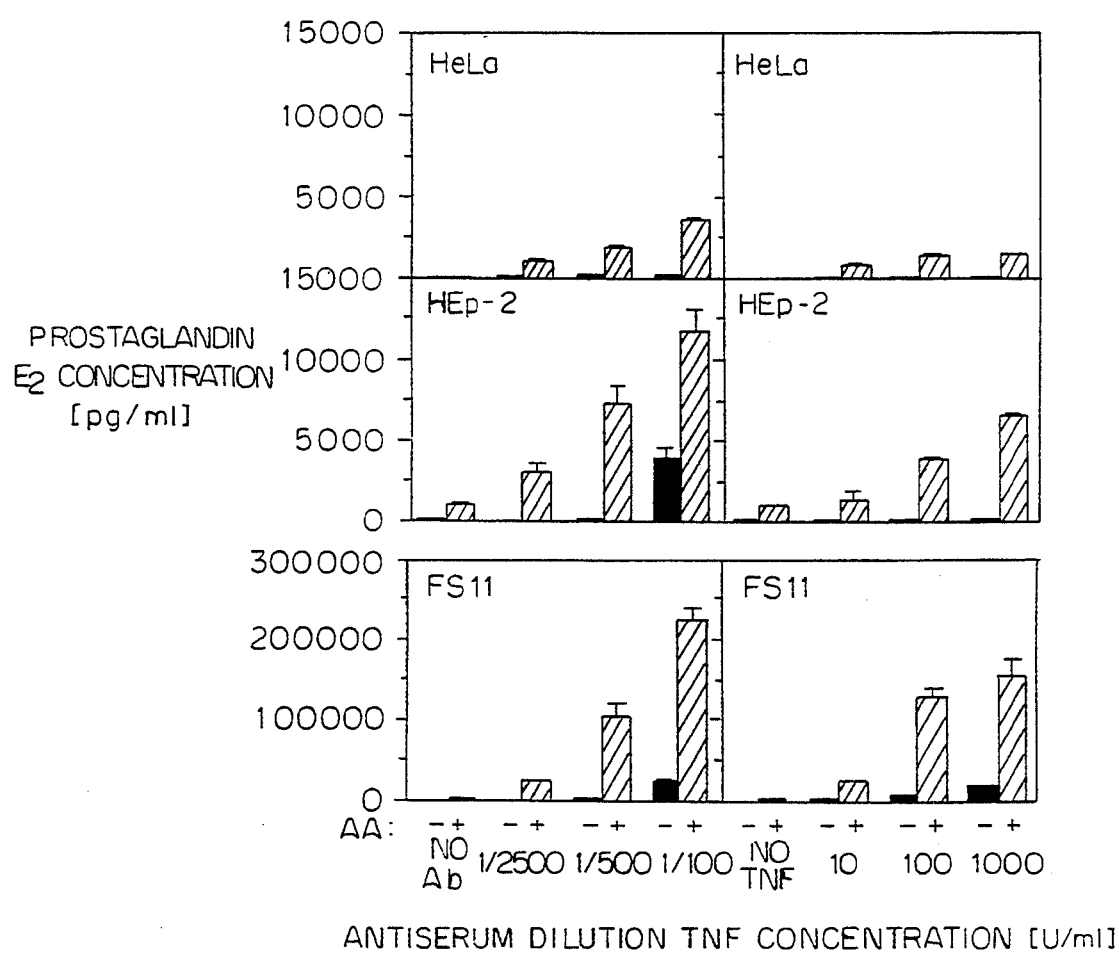
FIG. 6 shows the enhancement of $PGE_2$ synthesis by the antibodies to TBP-I and by TNF in different cell lines.

Cells were seeded in 96-well microtiter plates ($5 \times 10^4$ cells/well). Ten hours thereafter TNF and the antibodies were applied in serial dilutions. After further incubation for 15 hr at 37° C., the cell growth medium was collected and replaced with fresh medium containing arachidonic acid ($5 \times 10^{-5}$M). One hour later, the medium was collected again. The PGE$_2$ content of all samples was determined by an immuno-assay as described by Kaever et al., *Prostaglanding*, 35: 885–902, 1988. FIG. 6 shows the enhancement of PGE$_2$ synthesis by the antibodies to TBP-I and by TNF in HeLa, HEp-2 and FS11 cells and its augmentation by arachidonic acid (AA, 5 μM).

c. Stimulation of fibroblast growth

Growth stimulation in fibroblasts due to TNF and the antibodies to TBP-I was determined essentially as described by Viloek et al., *J. Exp. Med.*, 163: 632–643, 1986. Human foreskin fibroblasts (strain FS11, passage 10-12) were seeded in 96-well microtiter plates ($10^4$ cells/well). Either TNF, or the antibodies to TBP-I, were applied 18 h later. The rate of thymidine incorporation into the cells after 3 days of further incubation was determined by applying $^3$H-thymidine to the cells (1 μCi/well) and incubating them for another 16 h. The cells were then rinsed once with cold PBS, detached with trypsin, and the amount of label incorporated was determined by harvesting the cells onto glass fiber filters followed by liquid scintillation counting.

Figure 7A:
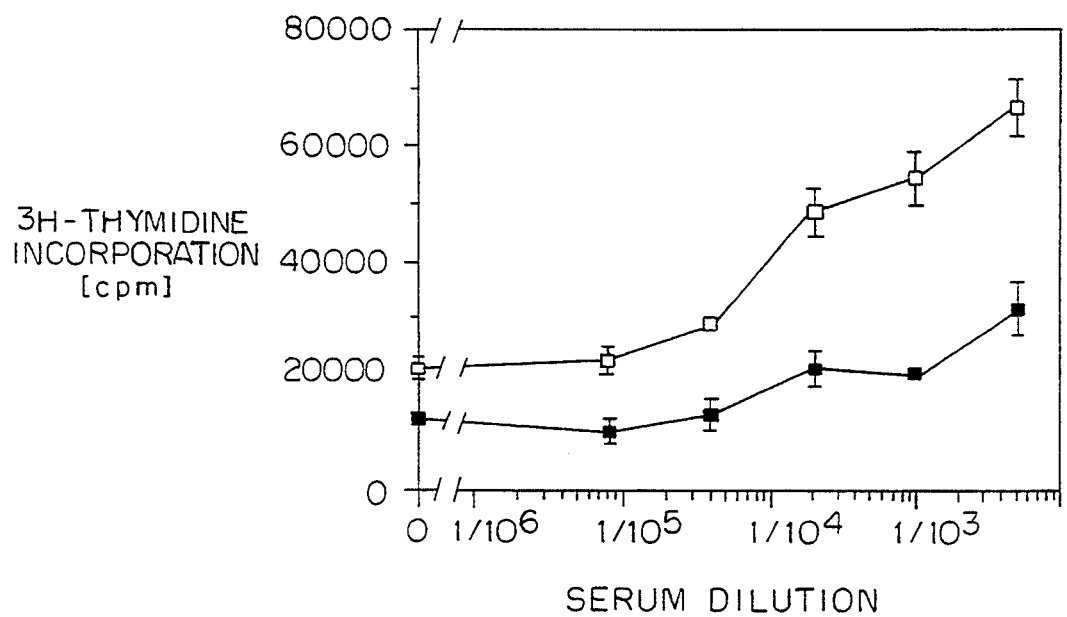
FIGS. 7A and 7B shows the growth stimulatory effect of the antibodies to TBP-I (A) and of TNF (B) on human fibroblasts and its reversion by IFN-gamma.
Figure 7B:
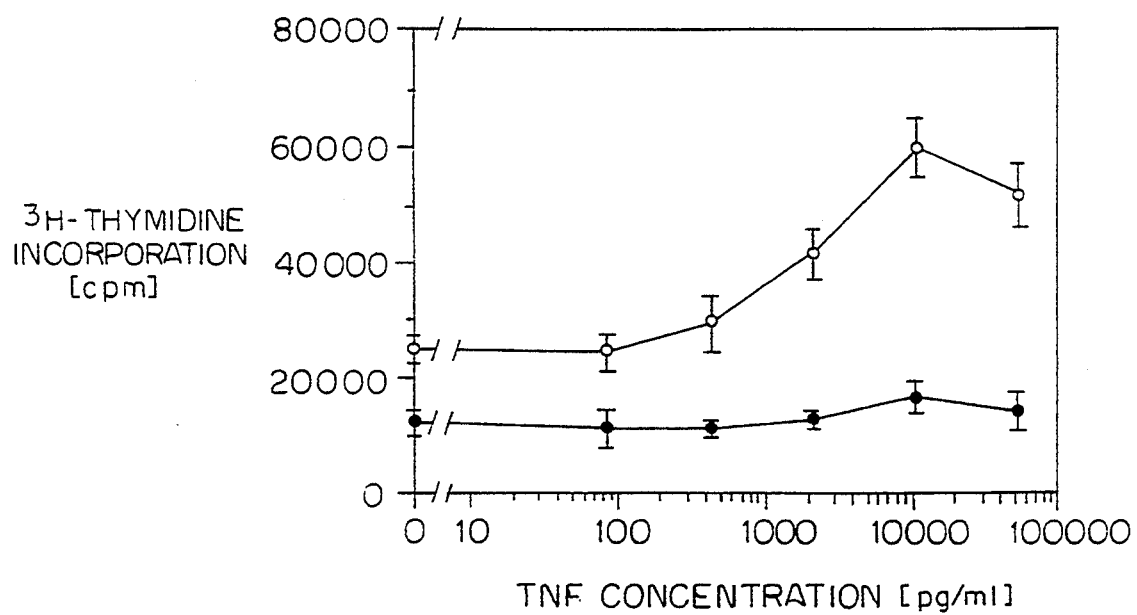

FIGS. 7A and 7B show the growth stimulatory effect of the antibodies to TBP-I (FIG. 7A) and of TNF (FIG. 7B) on human fibroblasts and its reversion by IFN-gamma. Human foreskin fibroblasts (strain FS11) were incubated for 3 days with the antibodies to TBP-I (□) or with TNF (o), in the presence (■,●) or absence (□,o) of IFN-gamma (250 U/ml). At the end of this incubation period the rate of $^3$H-thymidine incorporation was determined.

d. Inhibition of chlamvdial growth

The effect of the antibodies to TBP-I on growth of Chlamydia trachomatis (L$_2$434/Bu) in the HEp-2 cells was determined, as described for the antichlamydial effect of TNF by Shemer-Avni et al., *Infect. Immun*, 56:2503–2506, 1988. The antibodies were applied on the HEp-2 cells at the indicated concentration either alone or together with IFN-gamma; first, 1 day before infection with the chlamydiae and again, at the same concentrations, immediately after infection. The yield of chlamydiae 2 days after infection was determined using an immunoperoxidase assay for the chlamydial antigens and expressed as inclusion forming units/ml (IFU/ml).

Figure 8:
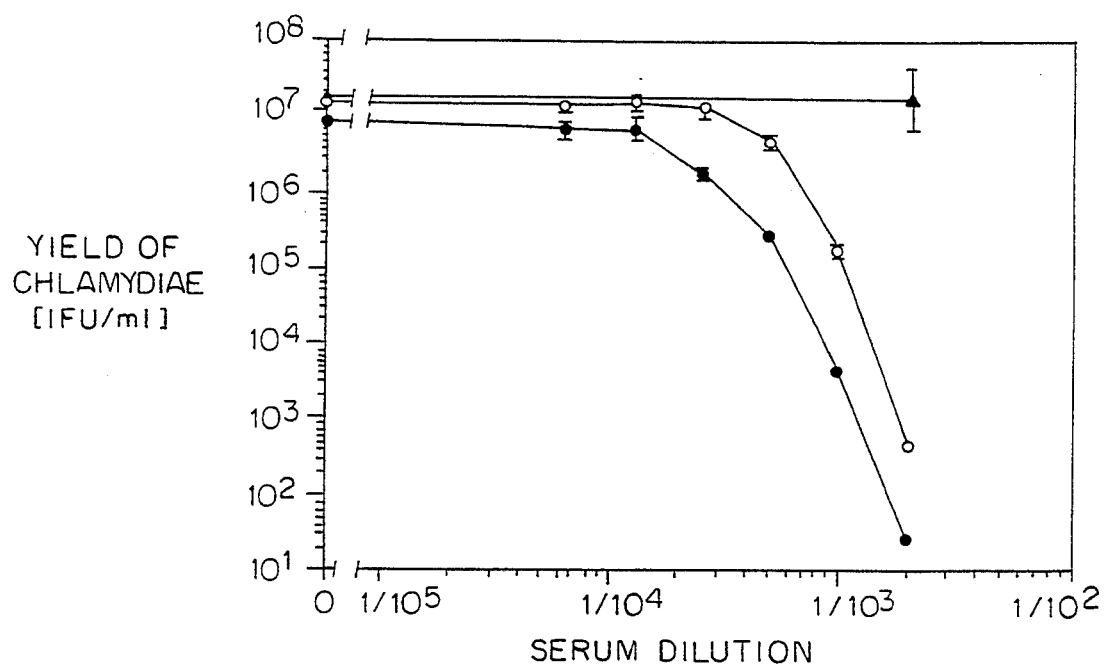
FIG. 8 shows the antichlamydial effect of the antiserum to TBP-I, enhancement of the effect by IFN-gamma and its abolition at a high tryptophan concentration.

FIG. 8 shows the antichlamydial effect of the antiserum to TBP-I, enhancement of the effect by IFN-gamma and its abolition at high tryptophan concentration. The effect of the antiserum, at the indicated dilutions, in the presence (●) or absence (o) of IFN-gamma (2 U/ml) was quantitated. Increase of tryptophan concentration, at the time of infection of the cells treated with anti-TBP-I from 10 μg/ml to 200 μg/ml abolished the antichlamydial effect (▲).

e. Antibodies to TBP-I have TNF-like effects

Applying the polyclonal antibodies to TBP-I on cells in the presence of the protein synthesis inhibitor cycloheximide (CHI) resulted, within a few hours, in extensive cytolysis. The cytocidal effect was complementin-dependent (data not shown) and appeared morphologically very similar to the cytocidal effect of TNF. If resembled the effect of TNF in several other respects as well:

(i) The sensitivity of different cell lines to polyclonal anti-TBP-I antibodies followed a similar pattern as their sensitivity to TNF. Thus, human foreskin fibroblasts (strain FS11) and HEp-2 cells, which are relatively resistant to TNF toxicity, were also much less sensitive to the toxicity of the antibodies (FIGS. 5A and 5B) (FIG. 5).

(ii) Like TNF, the antibodies failed to kill HeLa and SV80 cells in the absence of protein synthesis inhibitors (see cytotoxic activity under Section a above).

(iii) The sensitizing effect of protein synthesis inhibitors to the antibodymediated cell killing was largely dependent on the timing of their application. Maximal cytotoxity could be observed when the inhibitors and the antibodies were applied simultaneously. Application of the inhibitors a few hours after the antibodies resulted in significantly reduced cell death (Table II). The same time-dependence was observed for the sensitization by such inhibitors to the cytocidal effect of TNF (Table II). Thus the antibodies, like TNF, could be either cytotoxic to cells or induce in them resistance to their own toxicity, depending on whether they were applied in the presence or absence of protein synthesis inhibitors.

(iv) Resistance to both the toxicity of the antibodies and of TNF was induced in the SV80 cells also by pretreatment with IL-1 (Table III). Furthermore, the antibodies and TNF could induce in these cells cross resistance to each other's toxicity (Table III).

In the following tables, āTBP-I stands for antibodies to TBP-I.

TABLE II

Time-dependent sensitization of SV80 cells to the cytocidal effect of TNF or of antibodies to TBP-I, by CHI.

| Time of CHI application | TNF (100 u/ml) | ā TBP-I (1:200) |
|---|---|---|
| | Cell viability (%) | |
| Simultaneously with ā TBP-I/TNF | <1 | <1 |
| + 1 h | <1 | <1 |
| + 3 h | 41 | 48 |
| + 6 h | 77 | 73 |
| Not added | 100 | 100 |

SV80 cells were incubated for 16 h with TNF or with the antibodies to TBP-I (ā). CHI (50 μg/ml) was added to the culture at time zero or at 1, 3, or 6 h after application of TNF or of the antibodies (ā). Cell viability was determined at the end of the incubation period by the neutral red uptake method.

TABLE III

Induction of resistance to the cytocidal effects of ā TBP-I, or of TNF by TNF itself, ā TBP-I and IL-1

| | Pretreatment (for 6 h) | | | |
|---|---|---|---|---|
| Treatment | — | TNP (100 U/ml) | IL-1 (10 U/ml) | ā TBP-I (1:200) |
| | Cell viability (%) | | | |
| CHI (50 μg/ml) | 100 | 91 | 95 | 85 |
| TNF (10⁴ U/ml) + CHI | 8 | 82 | 82 | 71 |
| ā TBP-I (1:200) + CHI | 9 | 89 | 84 | N.D. |

N.D. Not determined
SV80 cells were treated for 1 h with TNF, IL-1, ā TBP-I or without additives and incubated further for 6 h in medium alone to allow full recovery of the TNF receptors (pretreatment). The cells were then incubated for 12 h with TNF or with ā TBP-I in the presence of CHI, or with CHI alone (treatment). While without any pre-treatment, most cells were killed when incubated with TNF or with ā TBP-I together with CHI, cells which were first incubated with TNF, IL-1 or ā TBP-I in the absence of CHI were largely resistant to subsequent treatment with TNF or ā TBP-I in the presence of CHI.

Further examination of the effect of antibodies to TBP-I, when applied on cells in the absence of protein synthesis blockers, revealed that under these conditions the antibodies mediated several non-cytocidal TNF-like effects. In the foreskin fibroblasts and HEp-2 cells, which are quite resistant to TNF-cytotoxicity, as well as in the TNF sensitive HeLa cells, the antibodies, similarly to TNF had a marked stimulatory effect on the synthesis of PGE$_2$ (FIG. 6). The effect of both was particularly prominent when arachidonic acid was added to the cells, suggesting that in both cases it reflects an increase, not in the release of arachidonic acid, but in its conversion to prostaglandin. An additional TNF-like effect of the antibodies in the foreskin fibroblasts was an enhancement of the incorporation of thymidine (FIGS. 7A and 7B), apparently reflecting stimulation of cell growth. Like the growth stimulatory effect of TNF, the stimulation of fibroblast growth by the antibodies was obliterated when the cells were treated simultaneously with IFN-gamma (FIGS. 7A and 7B).

In HEp-2 cells, TNF suppresses the growth of chlamydiae, obligate parasitic bacteria which grow intracellularly within membrane bound structures. As shown in FIG. 8, growth of chlamydiae in these cells was also markedly inhibited by the antibodies to TBP-I. Inhibition of chlamydial growth by TNF is synergistic with the antichlamydial effect of IFN-gamma and is largely abrogated when the HEp-2 cells are grown in the presence of increased concentrations of tryptophan. The antichlamydial effect of the antibodies to TBP-I was affected by IFN-gamma and tryptophan in a similar manner (FIG. 8).

f. The TNF-like activity of the antibodies to TBP-I correlates with their ability to crosslink the TNF receptor molecules To explore the mechanisms for the TNF-like activity of antibodies to TBP-I, we tested the effect of monovalent F (ab) fragments of anti-TBP-I on cell function. Like the intact antibodies, the monovalent fragments effectively blocked the binding of radiolabelled TNF to cells, suggesting that they maintained the ability to bind to the cell surface TNF receptors (EC$_{50}$ was about 0.8 μg/ml for the intact antibodies and 1 μg/ml for the monovalent fragments). However, while in their intact form the antibodies were cytotoxic to CHI-treated SV80 cells at concentrations as low as 0.1 μg/ml, the monovalent F(ab) fragments of the antibodies did not exhibit any toxic effects (FIG. 9A). Indeed, by virtue of their ability to inhibit the binding of TNF to cells, the monovalent F(ab) fragments not only failed to kill the SV80 cells, but even had some inhibitory effect on their killing by TNF (FIG. 9C).

To check whether this loss of TNF-like activity in the fragmented antibodies was related to their monovalence we performed experiments to determine whether cross-linking of the F(ab) fragments would result in resurgence of their cytotoxic activity. It has been shown before that pulse-treatment of SV80 cells with TNF at 4° C., followed by incubation with CHI at 37° C., is sufficient to cause effective cell death. The intact antibodies to TBP-I were also cytotoxic under these conditions (compare solid and empty circles in FIG. 9A), while monovalent F(ab) fragments were not cytotoxic. However, when the F(ab)-pretreated cells were treated subsequently with goat antibodies to rabbit Ig to elicit cross-linking of the cell-bound antibody fragments, extensive cell death occurred (FIGS. 9B, 10).

FIG. 9A shows the lack of cytocidal activity of monovalent F(ab) fragments of the antibodies to TBP-I (◇), and the cytocidal effect of the anti-TBP-I immunoglobuline (o) at different concentrations, when applied to SV80 cells for 16 h together with CHI (50 μg/ml), and of "pulse" treatment with the anti-TBP-I immunoglobulins (●). Titration of the cytocidal effect of "pulse" treatment with the anti-TBP-I immunoglobulins was performed as follows: The cells were incubated with the antibodies, at the indicated concentrations, for 2 h at 4° C., rinsed and incubated further at 37° C. with CHI (50 μg/ml) with no further addition of the antibodies.

FIG. 9B shows the effect of goat antibodies to rabbit immunoglobulins when applied to SV80 cells which had been "pulse" treated with monvalent F(ab) fragments of the anti-TBP-I (●) or to untreated cells (o) (5 μg/ml). The "pulse" treatment with the F(ab) fragments was performed as described above for the intact immunoglobulins in FIG. 9A.

FIG. 9C shows the protection from TNF cytotoxicity by the monovalent fragments of the antibodies to TBP-I: SV80 cells which were "pulse" treated with the F(ab) fragments, as in FIG. 9B and, for comparison, cells treated in the same way with medium alone were further incubated for 16 h with TNF, at various concentrations, together with CHI (50 μg/ml).

FIGS. 10A through 10D show the morphology of SV80 cells after "pulse" treatment with monovalent F(ab) fragments of anti-TBP-I and further incubation in the presence or absence of anti immunoglobulin antibodies. Anti-TBP-I immunoglobulins and their monovalent F(ab) fragments were applied to the SV80 cells for 2 hr in the cold at a concentration of 3 μg/ml followed by rinsing and incubation for 16 hr at 37° C. in the presence of CHI with or without goat anti-rabbit IgE (4.5 μg/ml). All other conditions of the assay were as for FIG. 7A and 7B. Photographs were taken at a magnification of x125 after staining the cells with neutral red.

EXAMPLE 6: Monoclonal antibodies to TBP-I

Production of the monoclonal antibodies

Female Balb/C mice (8 weeks old) were injected with 1 μg purified TBP-I in an emulsion of complete Freund's adjuvant into the hind foot pads, and three weeks later, subcutaneously into the back in incomplete Freund's adjuvant. The other injections were given in weekly intervals, subcutaneously in PBS, Final boosts were given 4 days (i.p) and 3 days (i.v.) before the fusion with 9.0 μg of TBP-I in PBS. Fusion was performed using NSO/Mr cells and lymphocytes prepared from both the spleen and the local lymphocytes of the hind legs as fusion partners. The hybridomas were selected in DMEM supplemented with HAT, 15% horse serum and gentamycin 2 μg/ml. Hybridomas that were found to produce antibodies to TBP-I were subcloned by the limiting dilution method and injected into Balb/C mice that had been primed with pristane for the production of ascites. Immunoglobulins were isolated from the ascites by ammonium sulfate precipitation (50% saturation) and then dialyzed against PBS containing 0.02% azide. Purity was approximately 60% as estimated by analysis on SDS-PAGE and staining with coomassie blue. The isotypes of the antibodies were defined with the use of a commercially available ELISA kit (Amersham, U.K.).

Several positive clones were obtained for further studies and characterized. Some of the isolated subclones with their isotype and binding of TBP-I in inverted RIA are listed in Table IV. The isotypes and other characteristics of the monoclonal antibodies are given in FIG. 11.

Hybridomas TBP-I 18-1 and TBP-I 34-6 were deposited with the Collection Nationale de Cultures de Microorganismes, Institut Pasteur (CNCM), 25, rue du Docteur Roux, 75724 Paris CEDEX 15, France on March 12, 1990 and were assigned No. I-926 and No. I-927, respectively.

TABLE IV

| Subclones producing monoclonal antibodies to TBP-I | | | |
|---|---|---|---|
| Clone number | Screening with iRIA [CPM] | Screening of subclone with iRIA [CPM] | Isotype |
| 7.5 | 10000 | 2900 | IgG$_{2a}$ |
| .8 |  | 2800 | IgG$_{2a}$ |
| .9 |  | 5200 | IgG$_{2a}$ |
| 8.1 | 13440 | 10800 | IgG$_1$ |
| .3 |  | 11300 | IgG$_1$ |
| .11 |  | 11000 | IgG$_1$ |
| 13.2 | 28300 | 13800 | IgG$_{2a}$ |
| .3 |  | 15000 | IgG$_{2a}$ |
| .5 |  | 12900 | IgG$_{2a}$ |
| 14.6 | 17000 | 5400 | IgG$_{2a}$ |
| .7 |  | 6200 | IgG$_{2a}$ |
| .13 |  | 5700 | IgG$_{2a}$ |
| 16.1 | 29000 | 18000 | IgG$_{2a}$ |
| .3 |  | 16000 | IgG$_{2a}$ |
| .7 |  | 17500 | IgG$_{2a}$ |
| 17.2 | 7076 | 2100 | IgG$_{2a}$ |
| .7 |  | 2100 | IgG$_{2a}$ |
| .9 |  | 2200 | IgG$_{2a}$ |
| 18.1 | 28000 | 28800 | IgG$_{2b}$ |
| .2 |  | 27200 | IgG$_{2b}$ |
| .3 |  | 29800 | IgG$_{2b}$ |
| 20.2 | 46000 | 29800 | IgG$_{2a}$ |
| .5 |  | 32800 | IgG$_{2a}$ |
| .11 |  | 31400 | IgG$_{2a}$ |
| 23.1 | 5300 | 1700 | IgG$_{2a}$ |
| .3 |  | 1500 | IgG$_{2a}$ |
| .5 |  | 1900 | IgG$_{2a}$ |
| 29.1 | 4900 | 1600 | IgG$_{2a}$ |
| .4 |  | 1200 | IgG$_{2a}$ |
| .5 |  | 1100 | IgG$_{2a}$ |
| 30.1 | 48000 | 26700 | IgG$_{2a}$ |
| .3 |  | 27500 | IgG$_{2a}$ |
| .5 |  | 26700 | IgG$_{2a}$ |
| 34.6 | 29000 | 32800 | IgG$_{2a}$ |
| .7 |  | 34200 | IgG$_{2a}$ |
| .12 |  | 32300 | IgG$_{2a}$ |
| 39.1 | 4400 | 31800 | IgG$_{2a}$ |
| .6 |  | 31700 | IgG$_{2a}$ |
| .8 |  | 31500 | IgG$_{2a}$ |
| 68.1 | 46700 | 28900 | IgG$_{2a}$ |
| .4 |  | 28000 | IgG$_{2a}$ |
| .6 |  | 27500 | IgG$_{2a}$ |
| 79.6 | 2100 | 5000 | IgG$_{2a}$ |
| .7 |  | 1900 | IgG$_{2a}$ |
| .8 |  | 1900 | IgG$_{2a}$ |
| 80.1 | 2200 | 1900 | IgG$_{2b}$ |
| .4 |  | 2100 | IgG$_{2b}$ |
| .13 |  | 1800 | IgG$_{2b}$ |
| 83.2 | 1400 | 1600 | IgG$_{2a}$ |
| .7 |  | 1700 | IgG$_{2a}$ |
| .9 |  | 1600 | IgG$_{2a}$ |
| 86.1 | 2300 | 1500 | IgG$_{2a}$ |
| .7 |  | 1400 | IgG$_{2a}$ |
| .8 |  | 1600 | IgG$_{2a}$ |
| 91.2 | 1700 | 1900 | IgG$_{2a}$ |
| .3 |  | 1500 | IgG$_{2a}$ |
| .6 |  | 1600 | IgG$_{2a}$ |
| 92.1 | 2600 | 1900 | IgG$_{2a}$ |
| .2 |  | 1600 | IgG$_{2a}$ |
| .6 |  | 1500 | IgG$_{2a}$ |

EXAMPLE 7: Inverted Radioimmunoassay (iRIA) for the detection of the Monoclonal Antibodies to TBP-I This assay was used for estimating the level of the anti-TBP antibodies in the sera of the immunized mice and for screening for the production of the antibodies by hybridomas. PVC, 96-well microtiter plates (Dynatech 1-220-25) were coated for 12 hr at 4° C. with affinity purified goat anti mouse F(ab) immunoglobulins (Biomakor, Israel 10 μg/ml in PBS containing 0.02% NaN$_3$), then blocked for 2 hr at 37° C. with 0.5% BSA in PBS supplemented with 0.05% Tween 20 (Sigma) and 0.02% NaN$_3$ (blocking buffer) and washed 3 times with PBS containing 0.05% Tween 20 and 0.02% NaN₃ (washing buffer). Serum samples, in serial dilutions, or samples of hybridoma growth media (50 μl) were applied into the wells for 2 hr at 37° C. The plates were rinsed with washing buffer and $^{125}$I-labelled TBP-I (10,000 cpm, in blocking buffer) was applied into the wells. After further incubation of 2 hr at 37° C., the plates were washed and the amount of label which bound to individual wells was determined in the gamma-counter.

Figure 11:
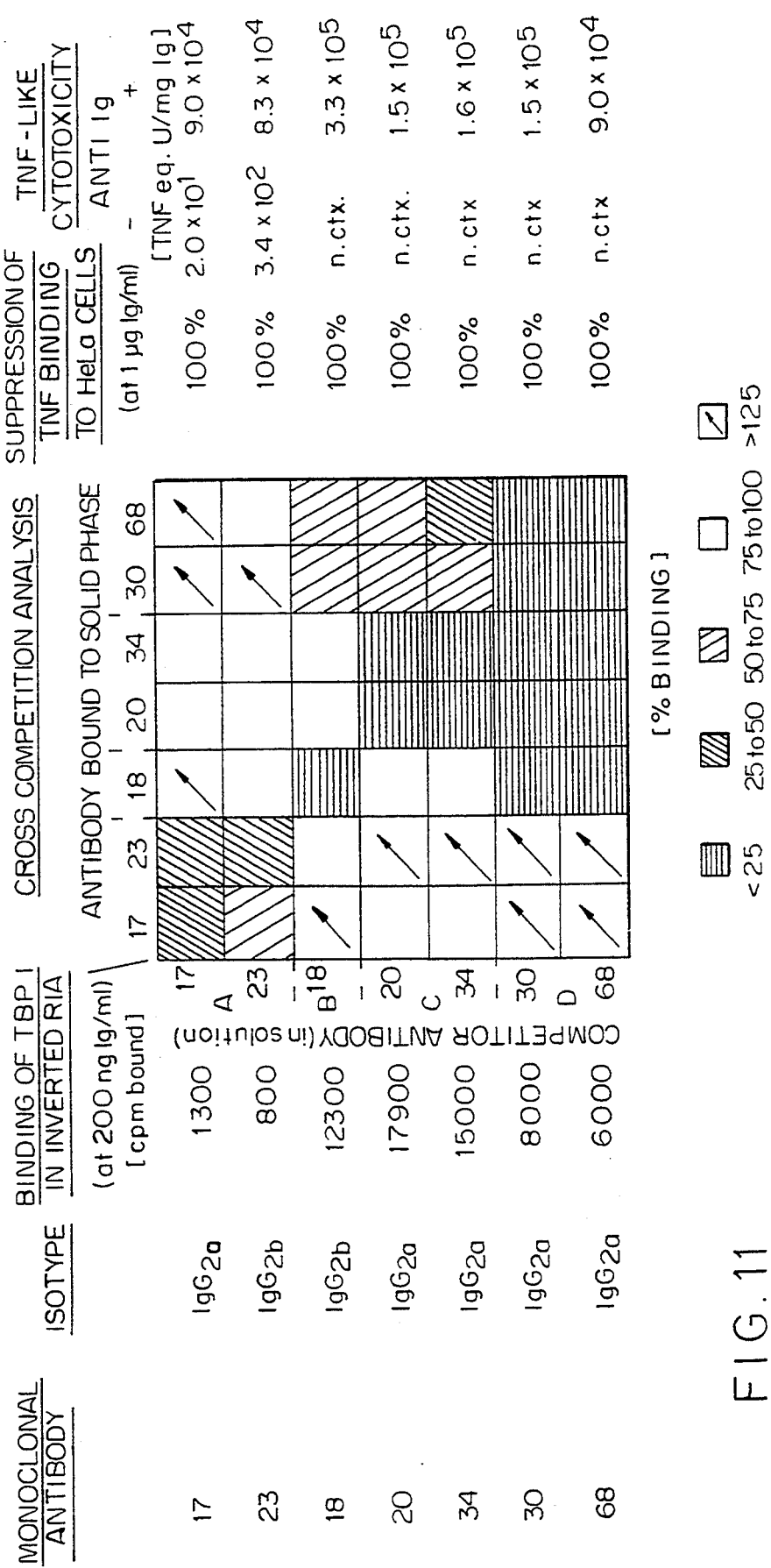
FIG. 11 shows the epitope mapping of TBP-I by cross-competition analysis with different monoclonal antibodies and correlation with the ability of the antibodies to suppress binding of TNF to HeLa cells and to mediate TNF-like cytotoxicity.

EXAMPLE 8: Epitope mapping of TBP-I by Cross Competition Analysis with Monoclonal Antibodies Polyvinylchloride (PVC), 96-well microtiter plates were coated, as described above, with purified monoclonal antibodies (mAbs) to TBP-I (25 μg/ml) and, following rinsing and blocking, samples of $^{125}$I-labeled TBP-I (50,000 cpm per well) which had been pre-incubated for 2 hr, at 37° C., with the same or another monoclonal antibody to TBP-I (at 1 μg/ml) were put into the wells. The plates were incubated overnight at 4° C., washed and the radioactivity bound to each well was determined in the gamma-counter. The results in FIG. 11 are expressed in percent of the control well where TBP-I was allowed to bind in the absence of competing mAbs. FIG. 11 shows the epitope mapping of TBP-I by cross competition analysis with 7 different mAbs to TBP-I and correlation with the ability of the antibodies to suppress binding of TNF to HeLa cells and to mediate TNF-like cytotoxicity. Binding of radiolabelled TBP-I to the mAbs (applied at saturating concentration, 200 ng/ml) in the inverted RIA, cross competition analysis of the mAbs for their binding to TBP-I and determination of the effect of the mAbs on the binding of TNF to HeLa cells were carried out as described. The TNF-like cytotoxicity of the antibodies was measured in two ways. In the first, (-anti Ig), SV80 cells were incubated 16 hr at 37° C. with the mAbs in the presence of CHI (50 μg/ml). In the second, (+anti Ig), the effect of crosslinking by anti-immunoglobulin antibodies on the cytotoxicity of the mAbs was tested. In this case, the SV80 cells were pulse-treated with the antibodies (2 hr at 4° C.), rinsed, and further incubated (16 hr at 37° C.) with rabbit anti-mouse $F(ab)_2$ antibodies (+ anti Ig) in the presence of CHI. Cell viability was determined by the neutral red uptake method. The cytotoxic activity of the antibodies is expressed in TNF equivalent units per mg immunoglobulin, where one TNF equivalent unit is defined as the amount of antibody exerting the same cytotoxicity as 1 U/ml TNF (16 pg/ml) (n.ctx - not cytotoxic).

The epitope mapping of TBP-I by cross competition analysis with the 7 mAbs suggests that these antibodies bind to four topologically distinct areas on the molecule (A - defined by mAbs 17 and 23, B - by 18, C - by 20 and 34, and D - by 30 and 68 (FIG. 11). An exceptional competition pattern was observed for the antibodies associated with epitope region D. The antibodies not only competed effectively with each other but also with the antibodies belonging to regions B and C. Moreover, the antibodies defining regions B and C competed, although less effectively, with the antibodies which bind to epitope D. One possible interpretation for this phenomenon is that epitopes B and C, while spatially distinct, overlap both with the epitope region represented by group D. An alternative possibility is that binding of an antibody to the epitope region D imposes a conformational change on TBP-I which prevents the binding of the antibodies recognizing determinants in B and C. The latter hypothesis seems consistent with the fact that the antibodies defining epitope D were the only ones found to recognize TBP-I after its denaturation with SDS in the presence of B-mercaptoethanol (not shown).

When applied to HeLa cells, the seven monoclonal antibodies to TBP-I described above, as well as ten other monoclonal antibodies to TBP-I all had a marked inhibitory effect on TNF binding (FIG. 11), implying that all the different epitopes which they recognize in the TBP-I molecule are also present in the call surface receptors for TNF.

The effect of the antibodies on binding of TNF to HeLa cells was performed as follows: HeLa cells were seeded into 15 mm tissue culture plates at a density of $2.5\times10^5$ cells/well. After 24 h incubation at 37° C. in 5% $CO_2$ atmosphere, the cells were transferred to ice, the growth medium was removed and the antibodies, diluted in PBS containing 0.5% BSA and 0.1% sodium azide, were applied to the cells for 2 h. The cells were then rinsed and tested for binding of TNF.

EXAMPLE 9: TNF-like Effect of Monoclonal Antibodies to TBP-I

To obtain additional information on the molecular requirements needed to trigger TNF-like biological activities with antibodies to TBP-I, we examined whether mAbs against TBP-I mediated TNF-like cytotoxicity. Two experimental approaches were taken: in the first, the antibodies were tested for cytotoxicity on SV80 cells without any further treatment (FIG. 11, −anti Ig) and in the second the cytotoxicity of the mAbs was tested after crosslinking them with anti-mouse immunoglobulin antibodies (FIG. 11, +anti Ig). As noted above, all mAbs tested appeared to bind to the class I TNF receptors, yet only two of the 17 mAbs had mild cytotoxic activity on SV80 cells. This difference in biological activity among the mAbs could not be correlated with their isotype nor with their binding capacity in the inverted RIA (FIG. 11). It did appear, however, to relate to the site of binding of the antibodies on the receptor molecule. In cross-competition analysis the two cytotoxic antibodies were found to bind to the same epitope region in TBP-I. None of the other antibodies bound to it (A in FIG. 11). Retesting the effect of the antibodies after cross linking them with anti-immunoglobulin antibodies, we found them all to be highly cytotoxic, to an extent which appeared roughly proportional to the effectiveness at which they bound TBP-I (compare in FIG. 11: cytotoxicity+anti Ig to the binding to TBP-I in inverted RIA).

Testing whether different mAbs to TBP-I can supplement each other in mediating TNF-like cytotoxicity we found that mixtures of two mAbs mapping to different epitope regions on TBP-I were highly cytotoxic to SV80 cells. For example, mixtures of the mAb 18 (epitope region B), which is not cytotoxic by itself, with the non-cytotoxic mAb 20 or 34 (both epitope region C) exerted strong cytotoxicity (app. $3\times10^5$ TNF eq. U/mg Ig; see FIG. 11 for definition of unitage). Mixtures of two mAbs mapping to the same epitope region were not more cytotoxic than each mAb alone.

EXAMPLE 10: The Use of anti-TBP-I antibodies for affinity chromatography

Antibodies to TBP-I can be utilized for the purification of TBP-I by affinity chromatography, as illustrated below with monoclonal antibodies against TBP-I produced as described in Example 6.

The monoclonal antibodies for affinity chromatography were selected by testing their binding capacity for the radiolabeled antigen in a solid phase radio immunoassay. Ascites from all hybridomas was purified by ammonium sulfate precipitation at 50% saturation followed by extensive dialysis against PBS. PVC 96 well plates were coated with the purified McAbs as described in Example 9. After blocking the plates with PBS containing 0.5% BSA, 0.05% Tween 20 (Sigma) and 0.02% $NaN_3$, the wells were incubated with 50,000 cpm $^{125}I$-TNF for 2 h at 37° C., then washed and the radioactivity which had bound to each well was quantitated in the gamma-counter. The antibodies with the highest binding capacity were examined for their performance in immuno affinity chromatography.

Polyacryl hydrazide agarose was used as resin to immobilize the antibodies. The semipurified immunoglobulins were concentrated and coupled to the resin as specified by Wilchek and Miron, Methods in Enzymology 34:72–76, 1979. Three monoclonal antibodies against TBP-I, clones 16, 20, and 34 were tested in these experiments.

Antibody columns of 1 ml bed were constructed. Before use, all columns were subjected to 10 washes with the elution buffer, each wash followed by neutralization with PBS. Then the columns were loaded with 120 ml of concentrated urinary proteins in PBS with 0.02% $NaN_3$. The flow rate of the columns was adjusted to 0.2 to 0.3 ml per minute. After loading, the columns were washed with 50 ml PBS and then eluted with a solution containing 50 mM citric acid, pH 2.5, 100 mM NaCl and 0.02% $NaN_3$. Fractions of 1 ml were collected. Samples of the applied urinary proteins, the last portion of the wash (1 ml) and of each elution fraction (8 fractions of 1 ml per column) were taken and tested for protein concentration (Table V) and activity in the bioassay for TBP-I (Table VI). According to the protein measurements before and after coupling of the antibodies to hydrazide agarose, the following amounts of immunoglobulin had been bound to the columns:

Clone 16: 8.4 mg/ml agarose
Clone 20: 7.2 mg/ml agarose
Clone 34: 9.4 mg/ml agarose All protein measurements were done according to a micro-fluourescamin method in comparison to a standard solution containing 100 μg BSA/ml (Stein, S, and Moschera, J., Methods Enzymol, 79:7–16, 1981).

The results of bioactivity and protein concentrations of applied, last wash and elution fractions are summarized in tables V and VI.

TABLE V

| Protein Concentrations | | | |
|---|---|---|---|
| | Clone 16 [μg/ml] | Clone 20 [μg/ml] | Clone 34 [μg/ml] |
| Applied (120 ml) | 35800 | 35800 | 35800 |
| Unbound (120 ml) | 35700 | 35700 | 35700 |
| Last wash (1 ml) | 42 | 38 | 12 |
| Elution 1 (1 ml) | 47 | 38 | 45 |
| Elution 2 (1 ml) | 550 | 784 | 714 |
| Elution 3 (1 ml) | 151 | 150 | 194 |
| Elution 4 (1 ml) | 100 | 51 | 122 |
| Elution 5 (1 ml) | 32 | 24 | 35 |

The protein concentrations were determined by a micro-flurescamin method in comparison to a BSA standard (100 μg/ml)

TABLE VI

| Purification of TBP-I with monoclonal antibodies bound to hydrazide agarose | | | |
|---|---|---|---|
| | Clone 16 Bioassay [U/ml] | Clone 20 Bioassay [U/ml] | Clone 34 Bioassay [U/ml] |
| Applied | 210 | 210 | 210 |
| Unbound | 100 | 60 | 80 |
| Last wash | *<detect | <detect | <detect |
| Elution 1 | <detect | 850 | 1200 |
| Elution 2 | 4800 | 10100 | 19500 |
| Elution 3 | 3500 | <detect | <detect |
| Elution 4 | 2500 | <detect | <detect |
| Elution 5 | 1000 | <detect | <detect |

*Applied, unbound and last wash were assayed at a dilution of 1:20 and higher and the elution fractions at 1:200 and higher. Samples which gave no discernable signal at this dilution appear an "below detection" (<detect) in the table.

EXAMPLE 11: Determination of TBP-I using anti-TBP-I antibodies

The levels of TBP-I in the sera of healthy individuals, patients with cancer or systemic lupus erythematosus (SLE) and of pregnant women at term were determined by an ELISA method employing a monoclonal antibody to TBP-I coating the plates. 50 μl of each sample was added and after a 2.5 h incubation at 37° C. the wells were washed with a solution of PBS, Tween 0.05% and sodium azide 0.02%, after which a rabbit anti-TBP-I polyclonal antibody was added for 2.5 h at 37° C. Then the wells were washed again (no azide) and goat anti-rabbit horseradish peroxidase-coupled antibody was added for 2 h. Following this incubation, and washing, an ABTS buffer was added and optical density (O.D.) read 30 min. later at 600 nm.

The normal levels of TBP-I in human serum of healthy individuals as determined by the ELISA method are $0.3 \pm 0.13$ ng/ml.

Figure 12:
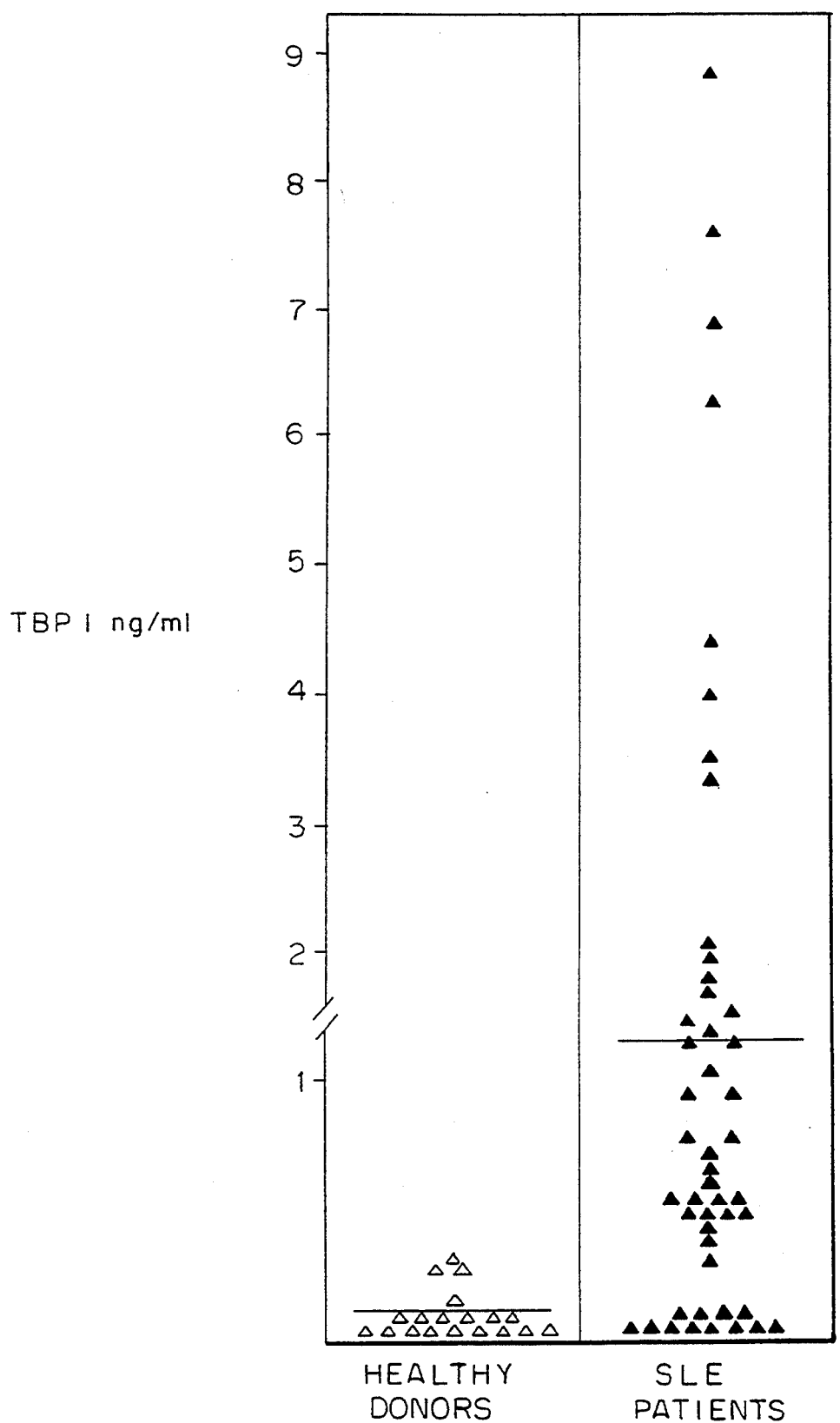
FIG. 12 shows the levels of TBP-I in the sera of healthy individuals and of systemic lupus erythematosus (SLE) patients.

In the sera of 46 patients with Systemic Lupus Erythematosus (SLE), the TBP-I levels were $1.5 \pm 1.2$ ng/ml, a value highly significant compared to the normal levels ($p<0.001$). As shown in FIG. 12, 36 out of the 46 patients with SLE had a TBP-I level higher than the mean$\pm$ 2SD of normal values. We found a highly significant correlation between the TBP-I levels and the disease activity index developed by Symmonds, D.P.M. et al, Quarterly J. of Med. (1988), Vol. 69, pp. 927–937: $r=0.62$, $p<0.01$. A similar correlation was found between TBP-I and the classical marker of SLE activity, the anti-DNA antibodies ($r=0.50$, $p<0.001$).

These results indicate that TBP-I may be useful as a sensitive marker of disease activity and a predictor of exacerbations in SLE patients, and thus may be useful in monitoring immune activation related to disease activity in these patients as well as in patients with other autoimmune diseases.

Figure 13:
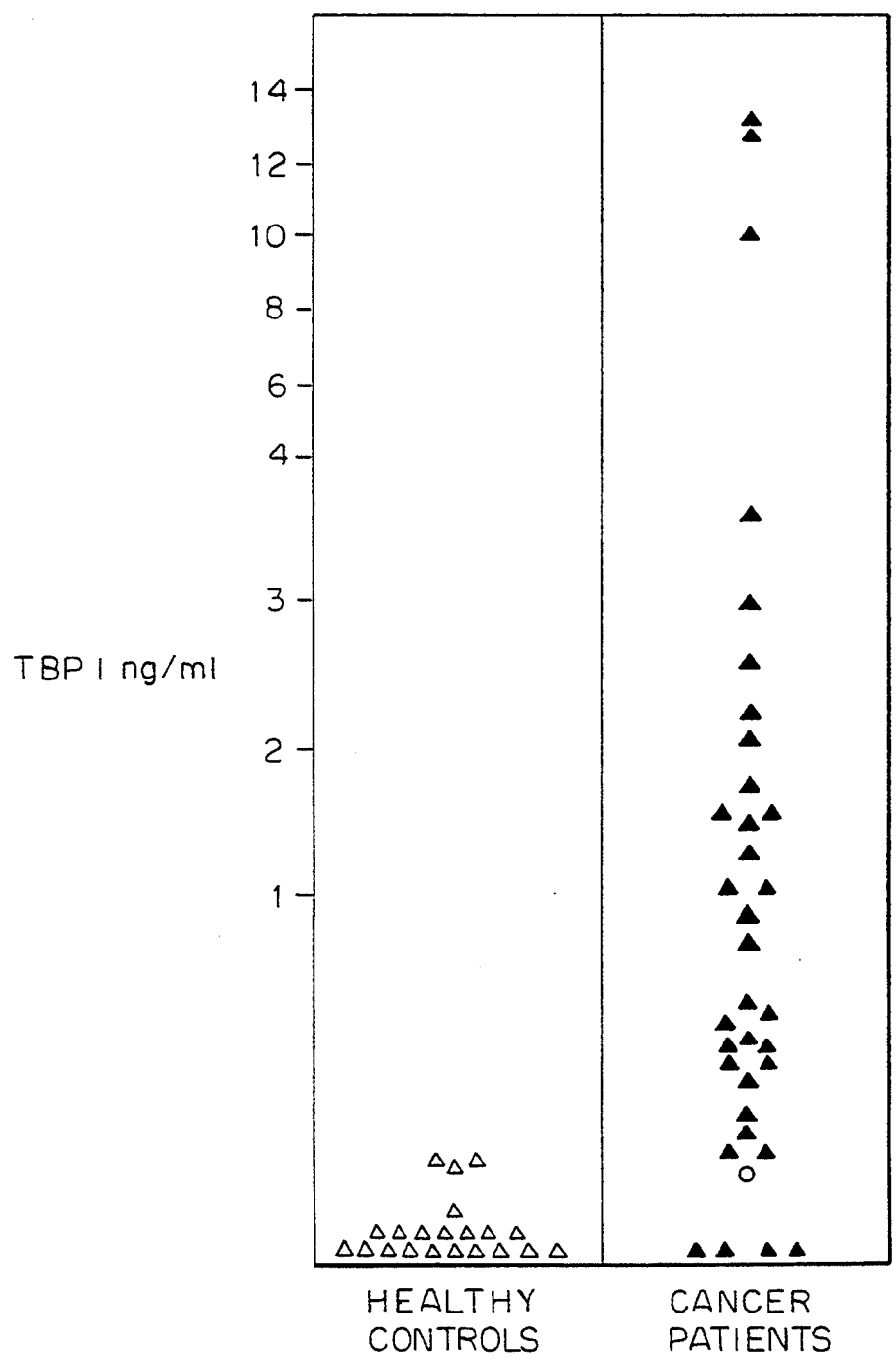
FIG. 13 shows the levels of TBP-I in the sera of healthy individuals and of cancer patients.

By the above ELISA method, the TBP-I levels in sera of patients with different types of cancer, were examined. In 20 out of 34 patients (58.8%) with different types of cancer, the TBP-I levels may be a mean $\pm$ 2SD. The difference between the TBP-I of cancer patients ($1.5 \pm 1.5$ ng/ml) and healthy controls ($0.3 \pm 0.13$ ng/ml) was highly significant statistically ($p<0.001$) - FIG. 13.

These results indicate that TBP-I may prove a useful and universal marker of different types of cancer and may be applied in early detection of this condition. After cancer resection, normalization of TBP-I levels may be a marker of cure of the disease. An increase in TBP-I, after initial normalization, may be an early and sensitive universal marker of disease relapse.

We claim:

1. An antibody to a human tumor necrosis factor binding protein designated TBP-I which specifically recognizes said protein.

2. An antibody as claimed in claim 1 which is further characterized in that it blocks the binding of TNF to HeLa and MCF7 cells, but does not block the binding of TNF to U937 cells.

3. An antibody according to claim 1 which is a polyclonal antibody.

4. An antibody according to claim 1 which is a monoclonal antibody.

5. A monoclonal antibody according to claim 4 produced from a hybridoma formed by fusion of myeloma cells with spleen cells of mice previously immunized with TBP-I.

6. An antibody in accordance with claim 1, wherein said antibody is an intact antibody.

* * * * *